(12) United States Patent
Schiemann et al.

(10) Patent No.: US 9,655,934 B2
(45) Date of Patent: May 23, 2017

(54) DERMATOLOGICALLY EFFECTIVE YEAST EXTRACT

(75) Inventors: Yvonne Schiemann, Essen (DE); Mike Farwick, Essen (DE); Thomas Haas, Muenster (DE); Mirja Wessel, Bochum (DE)

(73) Assignee: EVONIK DEGUSSA GMBH, Essen (DE)

( * ) Notice: Subject to any disclaimer, the term of this patent is extended or adjusted under 35 U.S.C. 154(b) by 518 days.

(21) Appl. No.: 14/128,244

(22) PCT Filed: Jun. 14, 2012

(86) PCT No.: PCT/EP2012/061263
§ 371 (c)(1),
(2), (4) Date: Dec. 20, 2013

(87) PCT Pub. No.: WO2013/000717
PCT Pub. Date: Jan. 3, 2013

(65) Prior Publication Data
US 2014/0127257 A1 May 8, 2014

(30) Foreign Application Priority Data
Jun. 29, 2011 (EP) .................... 11171953

(51) Int. Cl.
| | | |
|---|---|---|
| *A61K 36/06* | (2006.01) | |
| *A61K 36/062* | (2006.01) | |
| *A61K 36/064* | (2006.01) | |
| *A61K 8/99* | (2017.01) | |
| *A61Q 19/00* | (2006.01) | |
| *C12P 1/02* | (2006.01) | |
| *A23L 33/145* | (2016.01) | |

(52) U.S. Cl.
CPC .......... *A61K 36/064* (2013.01); *A23L 33/145* (2016.08); *A61K 8/99* (2013.01); *A61K 36/06* (2013.01); *A61Q 19/00* (2013.01); *C12P 1/02* (2013.01); *A23V 2002/00* (2013.01)

(58) Field of Classification Search
CPC ..... A61K 36/06; A61K 36/062; A61K 36/064
USPC ........................................................ 424/780
See application file for complete search history.

(56) References Cited

U.S. PATENT DOCUMENTS

| | | | | |
|---|---|---|---|---|
| 2006/0110815 A1* | 5/2006 | Gruber | ............... | C12N 1/063 435/254.2 |
| 2006/0234360 A1* | 10/2006 | Branduardi | ............. | C12P 17/04 435/126 |
| 2007/0134265 A1 | 6/2007 | Takada et al. | | |
| 2009/0117633 A1* | 5/2009 | Bradley | ................. | C12N 9/242 435/161 |
| 2010/0135481 A1* | 6/2010 | Frauenthal | ............... | H04B 3/23 379/406.06 |
| 2010/0324257 A1 | 12/2010 | Karau et al. | | |
| 2011/0118504 A1 | 5/2011 | Haas et al. | | |
| 2011/0189742 A1 | 8/2011 | Haas et al. | | |
| 2011/0257429 A1 | 10/2011 | Schraven et al. | | |
| 2013/0164797 A1 | 6/2013 | Gielen et al. | | |
| 2013/0323822 A1* | 12/2013 | Brevnova | .............. | C12N 15/52 435/254.21 |

FOREIGN PATENT DOCUMENTS

| | | |
|---|---|---|
| CN | 1921823 A | 2/2007 |
| CN | 101380288 A | 3/2009 |
| DE | 1165574 B | 3/1964 |
| DE | 3740186 A1 | 1/1989 |
| DE | 3938140 A1 | 8/1991 |
| DE | 4009347 A1 | 9/1991 |
| DE | 4238081 A1 | 7/1993 |
| DE | 4204321 A1 | 8/1993 |
| DE | 4324219 A1 | 1/1994 |
| DE | 4229707 A1 | 3/1994 |
| DE | 4229737 A1 | 3/1994 |
| DE | 4309372 A1 | 9/1994 |
| DE | 19855934 A1 | 6/2000 |
| EP | 0666732 A1 | 8/1995 |
| EP | 2 033 627 A2 | 3/2009 |
| JP | 2008520549 A | 6/2008 |
| JP | 2009108031 A | 5/2009 |
| WO | WO 2006/044482 A2 | 4/2006 |
| WO | 2009084742 A2 | 9/2009 |
| WO | 2010011885 A1 | 1/2010 |
| WO | WO 2010/087503 A1 | 8/2010 |
| WO | 2011025635 A2 | 3/2011 |

OTHER PUBLICATIONS

Souto, L. R. M., et al., "Model for human skin reconstructed in vitro composed of associated dermis and epidermis", Sao Paulo Med J., Mar. 2006, pp. 71-76, 124(2).
Reddy, S., et al., "Characterization of Wnt gene expression in developing and postnatal hair follicles and identifcation of Wnt5a as a target of Sonic hedgehog in hair follicle morphogenesis", Mechanisms of Development 107, Sep. 2001, pp. 69-82.
Pinney, E., et al., "Human Three-Dimensional Fibroblast Cultures Express Angiogenic Activity", Journal of Cellular Physiology 183, Apr. 2000, pp. 74-82.
Mosmann, T., "Rapid Colorimetric Assay for Cellular Growth and Survival: Application to Proliferation and Cytotoxicity Assays", Journal of Immunological Methods, 65, Dec. 1983, pp. 55-63, Elsevier.
Miller, J. R., "Protein family review The Wnts", Genome Biology, Dec. 28, 2001, 3(1), 15 pages.
"Kosmetische Färbemittel" [Cosmetic Colouring Agents] of the Farbstoffkommission der Deutschen Forschungsgemeinschaft [Colorant Commission of the German Research Association], Verlag Chemie, Weinheim, 1984, pp. 81-106.

(Continued)

*Primary Examiner* — Chris R Tate
(74) *Attorney, Agent, or Firm* — Scully, Scott, Murphy & Presser, P.C.

(57) ABSTRACT

The invention relates to a method for producing a dermatologically active yeast extract, comprising the following steps: providing a preculture of the yeast cells, culturing the cells for at least fifteen minutes at a pH of 1.8-4, harvesting the cells and lysing the cells, and a yeast extract produced thereby and products comprising said yeast extract.

8 Claims, 3 Drawing Sheets

(56) References Cited

OTHER PUBLICATIONS

Finkel, P., et al., "Formulierung Kosmetischer Sonnenschutzmittel", 1996, SÖFW—journal, vol. 122, p. 543, With English-Language Abstract.

Fu-Ping, L., et al., "Studies on Live Yeast Cell Derivative Induced by High Temperature and H2O2", Microbiology, Dec. 31, 2004, pp. 28-32, vol. 31, No. 5—English-language abstract.

Giannattasio, S. et al., Acid stress adaptation protects *Saccharomyces cerevisiae* from acetic acid-induced programmed cell death, Gene, (Jul. 18, 2005), vol. 354, pp. 93-98.

Hernandez-Montanez, Z. et al., The intracellular proteolytic system of Yarrowia lipolytica and characterization of an aminopeptidase, FEMS Microbiology Letters, (Mar. 2007), vol. 268, pp. 178-186.

English abstract only of United Kingdom Patent Publication No. GB 962919 A.

English abstract only of European Patent Publication No. EP 1005853 A1.

English abstract only of European Patent Publication No. EP 0297310 A2.

English abstract only of European Patent Publication No. EP 0555776 A1.

English abstract only of German Patent Publication No. DE 4237081 A1.

Translation of Japanese Office Action dated Jan. 29, 2016, received in a corresponding foreign application.

Berry, D. B., et al., "Stress-Activated Genomic Expression Changes Serve a Preparative Role for Impending Stress in Yeast", Molecular Biology of the Cell, Nov. 2008, pp. 4580-4587, vol. 19.

De Melo, H.F., et al., "Physiological and molecular analysis of the stress response to *Saccharomyces cerevisiae* imposed by strong inorganic acid with implication to industrial fermentations", Journal of Applied Microbiology ISSN, 2010, pp. 116-127, vol. 109.

Japanese Office Action dated Sep. 15, 2016 received in a corresponding foreign application and an English-language translation thereof.

* cited by examiner

DERMATOLOGICALLY EFFECTIVE YEAST EXTRACT

The invention relates to a method for producing a dermatologically active yeast extract, comprising the following steps: providing a preculture of the yeast cells, cultivating the cells for at least fifteen minutes at a pH of 1.8-4, harvesting the cells and lysing the cells, and a yeast extract produced thereby and products comprising said yeast extract.

The skin is the largest organ of the human body. Among its many functions, for example for heat control and as a sensory organ, its barrier function, which prevents drying out of the skin—and thus ultimately of the whole body—is certainly the most important. At the same time the skin acts as a protective device against the penetration and absorption of substances from outside. This barrier function is provided by the epidermis, which—as the outermost layer—forms the actual protective cover against the environment. With about a tenth of the total thickness, it is also the thinnest layer of the skin. The epidermis is a layered tissue, in which the outer layer, the horny layer (stratum corneum), is the important part for the barrier function.

Cosmetic skin care is to be understood primarily as reinforcing or restoring the natural function of the skin as a barrier against environmental factors (e.g. dirt, chemicals, microorganisms) and against loss of endogenous substances (e.g. water, natural fats, electrolytes). If this function is disturbed, there may be increased absorption of toxic or allergenic substances or attack by microorganisms, and consequently toxic or allergic skin reactions.

The aim of skin care is also to make up for the loss of fats and water from the skin caused by daily washing. This is particularly important when the natural capacity for regeneration is inadequate. In addition, skin care products should protect against environmental factors, especially sun and wind, and should delay skin ageing.

Products for the care of tired, especially aged skin are known per se. They contain e.g. retinoids (vitamin A acid and/or derivatives thereof) or vitamin A and/or derivatives thereof. However, their action on structural damage is limited in its extent. Furthermore, in product development, adequately stabilizing the active substances against oxidative breakdown poses considerable difficulties. Moreover, the use of products containing vitamin A acid often causes severe erythematous skin irritation. Tired skin is also often accompanied by a tendency to be overweight and/or by so-called cellulite with which it is often associated. Consumers' body awareness has definitely increased in recent years. In addition to cleaning and caring applications, steps are also increasingly being taken for improving the body silhouette. Cellulite—a widespread phenomenon—occupies a central position in this. The visible picture of cellulite is due to an increase in layers of subcutaneous fat, weakness of the connective tissue and a decrease in perfusion conditions in the blood and lymphatic systems. The cause is therefore a partly constitutional weakening of the connective tissue with simultaneous development of enlarged fat cell compartments as a result of being overweight, unbalanced nutrition, and lack of movement. The development of cellulite can also be attributed to increased permeability of the walls of the capillaries, which allows the penetration of water into the connective tissues.

Against this background, there is an increasing demand for agents whose application on the skin brings about alleviation or at least slowing of the adverse effects described, i.e. in particular has a firming and strengthening effect on the skin. Against the background of consumers' uncertainty with respect to genetic engineering techniques, there is a particular demand for corresponding agents that can be regarded, according to strict yardsticks, as purely biological, especially those that can be produced without using genetic engineering techniques and/or corresponding organisms.

WO2010087503 describes the biotechnological use of *Yarrowia* for producing succinate, but does not teach the use of *Yarrowia* extracts for dermatologically active agents.

The problem to be solved by the invention is to provide new dermatologically active agents, application of which on the skin counteracts the aforesaid effects, and methods for producing said agents. Furthermore, one of the problems to be solved by the invention is to develop a dermatologically active agent that is purely biological according to strict criteria, i.e. in particular one that is produced without using genetic engineering techniques or genetically modified organisms. Another problem to be solved by the present invention is to develop a dermatologically active agent that can be produced from renewable raw materials.

These and other problems are solved by the object of the present application and especially also by the object of the appended independent claims, wherein embodiments follow from the subclaims According to the invention, in a first aspect the problem is solved by a method for producing a dermatologically active yeast extract, comprising the following steps: a) providing a preculture of the yeast cells, c) culturing the cells for at least fifteen minutes at a pH from 1.8 to 4, d) harvesting the cells and e) lysing the cells.

In a first embodiment of the first aspect, the method further comprises step b) culturing the cells for at least one hour at a temperature from 34 to 39° C. and a pH>5.

In a second embodiment of the first aspect, which also represents an embodiment of the first embodiment, step e) is carried out using a water-based lysis agent.

In a third embodiment of the first aspect, which also represents an embodiment of the first and second embodiments, step b) is carried out first, and then step c).

In a fourth embodiment of the first aspect, which also represents an embodiment of the first to third embodiments, step c) is carried out at a temperature from 34 to 39° C.

In a fifth embodiment of the first aspect, which also represents an embodiment of the first to fourth embodiments, step b) takes 3 to 5 hours.

In a sixth embodiment of the first aspect, which also represents an embodiment of the first to fifth embodiments, step c) takes 45 to 75 minutes.

In a seventh embodiment of the first aspect, which also represents an embodiment of the first to sixth embodiments, steps b) and c) are carried out at a temperature from 36 to 38° C.

In an eighth embodiment of the first aspect, which also represents an embodiment of the first to seventh embodiments, step c) is carried out at a pH from 1.9 to 2.2.

In a ninth embodiment of the first aspect, which also represents an embodiment of the first to eighth embodiments, the yeast cell is a yeast cell from the group of genera that comprises *Yarrowia*, *Saccharomyces* and *Pichia*, and is preferably *Yarrowia*.

In a tenth embodiment of the first aspect, which also represents an embodiment of the first to ninth embodiments, step b) is carried out for 3 to 5 hours at a temperature from 36 to 38° C. and step c) at a pH from 1.9 to 2.2 and a temperature from 36 to 38° C. and for 45 to 75 minutes, and the yeast cells used are yeast cells of the genus *Yarrowia*.

According to the invention, in a second aspect the problem is solved with a yeast extract produced according to the first aspect or one of the embodiments of the first aspect.

According to the invention, in a third aspect, the problem is solved with a dermatologically active agent, which comprises a yeast extract from yeast cells of the genus *Yarrowia* or a yeast extract according to the second aspect of the present invention.

In a first embodiment of the third aspect of the present invention, the dermatologically active agent has skin and/or tissue finning action.

According to the invention, in a fourth aspect, the problem is solved with a food supplement that comprises a yeast extract according to the second aspect.

In a second embodiment of the third aspect, the dermatologically active agent comprises according to the third aspect or one of its embodiments or a food supplement according to the fourth aspect, wherein the proportion of protein in the yeast extract is 0.5 to 50 mg/l.

According to the invention, in a fifth aspect, the problem is solved with a method for cosmetic treatment of skin and/or hair, comprising topical application of the yeast extract according to the second aspect or a dermatologically active agent according to the third aspect or one of the embodiments of the third aspect.

According to the invention, in a sixth aspect, the problem is solved with a yeast extract according to the second aspect of the present invention for producing a medicinal product.

According to the invention, in a seventh aspect, the problem is solved with a yeast extract according to the second aspect of the present invention for producing a medicinal product against adiposity, diabetes, artherosclerosis, inflammatory diseases or cardiovascular diseases or for wound treatment.

According to the invention, in an eighth aspect, the problem is solved by using the yeast extract according to the second aspect of the present invention for in-vitro stimulation of the proliferation of keratinocytes, fibroblasts and/or adipocytes.

The present invention is based on the inventors' surprising finding that the use of alternative yeast strains and conditions permits the production of products that are dermatologically more active relative to conventional products. In particular the inventors found that yeast extracts based on strains of the genus *Yarrowia* surprisingly prove to be particularly effective. The inventors found, moreover, that the exposure of yeast cells generally and yeast cells of strains of the genus *Yarrowia* in particular to an environment with low pH is a suitable treatment for producing dermatologically active agents from said cells. Furthermore, the inventors of the present invention found that the dermatological efficacy of such agents can surprisingly be further improved by combining said exposure of said yeast cells to an environment with low pH with exposure to temperature stress, preferably in the order temperature stress and then pH stress. Finally, the inventors of the present invention found that the application of said yeast extracts on skin models, surprisingly, regulates the wnt-signal transduction pathway and the extracellular matrix of these cells and influences them in a manner that is advantageous for the physiology of the skin. Without wishing to be bound to a theory, the inventors of the present invention presume that the yeast cells of the genus *Yarrowia* release a dermatologically active extract because they have cell membrane proteins that interact particularly well with hydrophobic, high-fat substrates, and/or the cells comprise one or more hitherto unidentified factors that have a positive influence on the metabolism of skin cells.

The present invention comprises both extracts from *Yarrowia* cells, which have been stressed in every conceivable way, in particular by temperature, pH and oxidation stress. The invention further comprises yeast cells of any genus, stressed by extreme pH, preferably low pH. In a preferred embodiment they are cells of the genera *Saccharomyces, Pichia* and *Yarrowia*, and in a more preferred embodiment they are cells of the genus *Yarrowia*, especially of the strain *Yarrowia lipolytica*.

It is known from the prior art that yeast cells grow in an acidic environment, i.e. at pH below 7. Nonetheless, there are also limits for yeast cells, and starting from a certain pH, stress reactions develop, which are connected with the acidic medium. In a preferred embodiment, the term "pH stress", as used herein, means that the yeast cells are exposed to a pH that is below the pH that is optimum for their growth. In a more preferred embodiment this pH is in the range from 1.8 to 4. In an even more preferred embodiment the pH is in the range from 1.9 to 2.2. A person skilled in the art knows methods and protocols by which pH stress can be brought about, in the simplest case lowering of the nutrient medium by adding acid or harvesting the cells by centrifugation, followed by resuspension in a corresponding more acidic medium. The pH stress, especially in the form of step c) according to the first aspect of the invention, lasts in increasing order of preference, at least 20, 30, 45, 60, 75, 90, 120 or 180 minutes or lasts in increasing order of preference 20 to 180, 30 to 90, 45 to 75 or 50 to 70 minutes. During this time the pH is, in increasing order of preference, less than 5, 4.5, 4, 3.5, 3, 2.5 or 2.2 or is, in increasing order of preference, in the range from 1.8 to 5, 1.8 to 4, 1.9 to 3, 1.9 to 2.5, 1.9 to 2.2, 1.9 to 2.2, 2 to 2.8, 2 to 2.2 and most preferably it is 2.

In a preferred embodiment, the term "lysing" of cells, as used herein, means a method that is suitable for disrupting a cell, in the sense that its membrane becomes permeable and factors that are normally enclosed inside the cell can escape from the cell. A person skilled in the art knows suitable methods of lysis, for example using ultrasound or suitable commercially available equipment or suspension in low-salt buffers or distilled water.

The lysis of the yeast cells preferably takes place after the pH stress treatment using a water-based lysis agent. This term means, in a preferred embodiment, as used herein, that the lysis agent comprises mainly water as solvent. In another embodiment as hereunder it is understood that the solvent is something other than an alcohol. In another preferred embodiment the solvent is an alcohol, especially preferably propanediol. The yeast extract can be, in a respectively preferred embodiment, a total lysate or a solvent extract.

The inventors found, surprisingly, that the combination of temperature stress and pH stress has a particularly advantageous effect on the dermatological action of a yeast extract. In an especially preferred embodiment, the term "temperature stress", as used herein, means the incubation of a yeast cell at a temperature that is above the optimum temperature for growth. In increasingly preferred embodiments this temperature is higher than 33, 34, 35, 36, 37, 38 or 39° C. or is in the range from 34 to 42, 34 to 39, 35 to 38 or 36 to 38° C. In an especially preferred embodiment the temperature is 37° C. In an especially preferred embodiment the treatment of the yeast cell with a medium under pH stress is directly preceded by a treatment with temperature stress, i.e. the yeast cells are not given any opportunity to recover after the temperature stress. In other words step b) according to the first aspect of the present invention is followed immediately by step c), for example by adding acid to the medium in step b). In an especially preferred embodiment the stress-producing temperature in step c) is maintained, i.e. in step c) the yeast cell is exposed to a combination of temperature and pH stress. In another embodiment steps b) and c) can be in any order. In another preferred embodiment step c) takes place while step b) is still in progress; optionally steps b) and c) are initiated together.

In a preferred embodiment step b) is carried out for 3.5 to 4.5 hours at a temperature of 37° C. and step c) at a pH from 1.9 to 2.1 and a temperature from 36 to 38° C. and for 45 to 75 minutes, and the yeast cells used are yeast cells of the genus *Yarrowia*. In a preferred embodiment step b) is carried out for 2 to 6 hours at a temperature from 35 to 39° C. and step c) at a pH from 1.9 to 2.1 and a temperature from 36 to 38° C. and for 45 to 75 minutes, and the yeast cells used are yeast cells of the genus *Yarrowia lipolytica*.

The duration of the temperature stress step b) must be such that the cell is forced to adjust to the altered conditions that are unfavourable for it, especially through altered expression of proteins, for example of factors that improve resistance to the increased temperature. In an especially preferred embodiment, step b) takes, according to the first aspect of the present invention, in increasing order of preference at least 0.25, 0.5, 0.75, 1, 1.5, 2, 3 or 4 hours or lasts for 2 to 10, 3 to 6, 3 to 5, 3.5 to 4.5 hours.

The yeast extracts described in this application can be processed into dermatologically active care formulations, also designated synonymously and interchangeably as dermatological agent. In a preferred embodiment the term "dermatological agent", as used herein, means an agent for the non-medical treatment of the skin. In a preferred embodiment the yeast cell is a yeast cell from the group comprising the genera *Yarrowia*, *Saccharomyces*, *Kluyveromyces*, *Torulaspora*, *Schizosaccharomyces*, *Debaromyces*, *Candida*, *Pichia*, *Aspergillus* and *Penicillium*, even more preferably from the group comprising *Yarrowia*, *Saccharomyces* and *Pichia*. In an especially preferred embodiment the yeast cell is a yeast cell of the strain *Yarrowia lipolytica*.

The care formulations according to the invention contain from 0.001 wt % to 20 wt %, preferably 0.01 wt % to 5 wt %, especially preferably 0.05 wt % to 3, even more preferably 2 to 3 wt % of extract relative to the total weight of the care formulation.

The care formulations according to the invention can contain at least one additional component that is selected from the group comprising emollients, emulsifiers and surfactants, thickeners/viscosity controllers/stabilizers, UV-light protection filters, antioxidants and vitamins, hydrotropes (or polyols), solid materials and fillers, film formers, nacreous additives, deodorant and antiperspirant active substances, insect repellents, self-tanning agents, preservatives, conditioners, perfumes, colourants, biogenic active substances, care additives, overfatting agents and solvents.

As emollients, it is possible to use all cosmetic oils, especially mono- or diesters of linear and/or branched mono- and/or dicarboxylic acids with 2 to 44 carbon atoms with linear and/or branched saturated or unsaturated alcohols with 1 to 22 carbon atoms. The esterification products of aliphatic, bifunctional alcohols with 2 to 36 carbon atoms with monofunctional aliphatic carboxylic acids with 1 to 22 carbon atoms can also be used. Furthermore, long-chain aryl acid esters, e.g. esters of benzoic acid, e.g. benzoic acid esters of linear or branched, saturated or unsaturated alcohols with 1 to 22 carbon atoms, or also benzoic acid isostearyl esters or benzoic acid octyldocecyl esters are suitable. Other monoesters possibly suitable as emollients and oil components are e.g. the methyl esters and isopropyl esters of fatty acids with 12 to 22 carbon atoms, e.g. methyl laurate, methyl stearate, methyl oleate, methyl erucate, isopropyl palmitate, isopropyl myristate, isopropyl stearate, isopropyl oleate. Other suitable monoesters are e.g. n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate and esters that are obtainable from technical aliphatic alcohol fractions and technical aliphatic carboxylic acid mixtures, e.g. esters from unsaturated fatty alcohols with 12 to 22 carbon atoms and saturated and unsaturated fatty acids with 12 to 22 carbon atoms such as can be obtained from animal and vegetable fats. However, naturally occurring monoester or wax-ester mixtures such as are present e.g. in jojoba oil or in sperm oil, are also suitable. Suitable dicarboxylic acid esters are e.g. di-n-butyl adipate, di-n-butyl sebacate, di(2-ethylhexyl)adipate, di(2-hexyldecyl)succinate, D-isotridecylacelaat. Suitable diol esters are e.g. ethylene glycol dioleate, ethylene glycol-diisotridecanoate, propylene glycol-di-(2-ethylhexanoate), butanediol-diisostearate, butanediol-dicaprylate/caprate and neopentyl glycol dicaprylate. Other fatty acid esters that can be used as emollients are e.g. $C_{12-15}$ alkyl benzoate, dicaprylyl carbonate, diethylhexyl carbonate. Longer-chain triglycerides, i.e. triple esters of glycerol with three acid molecules, at least one of which is longer-chain, can also be used as emollients and oil components. For example, fatty acid triglycerides may be mentioned; as such, for example natural vegetable oils, e.g. olive oil, sunflower oil, soya oil, peanut oil, rape oil, almond oil, sesame oil, avocado oil, castor oil, cocoa butter, palm oil as well as the liquid fractions of coconut oil or palm kernel oil and animal oils e.g. shark-liver oil, cod-liver oil, whale oil, beef tallow and butterfat, waxes such as beeswax, carnauba wax, spermaceti, lanolin and neatsfoot oil, the liquid fractions of beef tallow or also synthetic triglycerides of caprylic-capric acid mixtures, triglycerides from technical oleic acid, triglycerides with isostearic acid, or from palmitic acid-oleic acid mixtures, can be used as emollients and oil components. Furthermore, it is also possible to use hydrocarbons, especially liquid paraffins and isoparaffins. Examples of hydrocarbons that can be used are paraffin oil, isohexadecane, polydecene, petroleum jelly, paraffinum perliquidum, squalane, ceresin. Furthermore, linear or branched fatty alcohols such as oleyl alcohol or octyldodecanol, and fatty alcohol ethers such as dicaprylyl ether, can also be used. Suitable silicone oils and waxes are e.g. polydimethylsiloxanes, cyclomethylsiloxanes, and aryl- or alkyl- or alkoxy-substituted polymethylsiloxanes or cyclomethylsiloxanes. Other oils that may be considered are for example Guerbet alcohols based on fatty alcohols with 6 to 18, preferably 8 to 10 carbon atoms, esters of linear $C_6$-$C_{22}$ fatty acids with linear $C_6$-$C_{22}$ fatty alcohols, esters of branched $C_6$-$C_{13}$ carboxylic acids with linear $C_6$-$C_{22}$ fatty alcohols, esters of linear $C_6$-$C_{22}$ fatty acids with branched $C_8$-$C_{18}$ alcohols, especially 2-ethylhexanol or isononanol, esters of branched $C_6$-$C_{13}$ carboxylic acids with branched alcohols, especially 2-ethylhexanol or isononanol, esters of linear and/or branched fatty acids with polyhydric alcohols (e.g. propylene glycol, dimeric diol or trimeric triol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, especially benzoic acid, vegetable oils, branched primary alcohols, substituted cyclohexanes, linear $C_6$-$C_{22}$ fatty alcohol carbonates, Guerbet carbonates, esters of benzoic acid with linear and/or branched $C_6$-$C_{22}$ alcohols (e.g. Finsolv™ TN), dialkyl ethers, ring-opening products of epoxidized fatty acid esters with polyols, silicone oils and/or aliphatic or naphthenic hydrocarbons.

Non-ionic, anionic, cationic or amphoteric surfactants can be used as emulsifiers or surfactants. Compounds from at least one of the following groups can be used as non-ionogenic emulsifiers or surfactants: addition products of 2 to 100 mol ethylene oxide and/or 0 to 5 mol propylene oxide on linear fatty alcohols with 8 to 22 carbon atoms, on fatty acids with 12 to 22 carbon atoms and on alkylphenols with 8 to 15 carbon atoms in the alkyl group, $C_{12/18}$ fatty acid mono- and diesters of addition products of 1 to 100 mol ethylene oxide on glycerol, glycerol mono- and diesters and sorbitan mono- and diesters of saturated and unsaturated fatty acids with 6 to 22 carbon atoms and ethylene oxide addition products thereof, alkyl mono- and oligoglycosides with 8 to 22 carbon atoms in the alkyl residue and ethylene oxide addition products thereof, addition products of 2 to 200 mol ethylene oxide on castor oil and/or hardened castor oil, partial esters based on linear, branched, unsaturated or saturated $C_6$-$C_{22}$ fatty acids, ricinoleic acid and 12-hydroxystearic acid and glycerol, polyglycerol, pentaerythritol, dipentaerythritol, sugar alcohols (e.g. sorbitol), alkyl glucosides (e.g. methylglucoside, butylglucoside, laurylglucoside) and polyglucosides (e.g. cellulose), mono-, di- and trialkylphosphates and mono-, di- and/or tri-PEG-alkylphosphates and salts thereof, polysiloxane-polyether copolymers (dimethicone copolyols), for example PEG/PPG-20/6 dimethicone, PEG/PPG-20/20 dimethicone, bis-PEG/PPG-20/20 dimethicone, PEG-12 or PEG-14 dimethicone, PEG/PPG-14/4 or 4/12 or 20/20 or 18/18 or 17/18 or 15/15, polysiloxane-polyalkyl polyether copolymers or corresponding derivatives, for example lauryl or cetyl dimethicone copolyols, especially cetyl PEG/PPG-10/1 dimethicone (ABIL® EM 90 (Evonik Goldschmidt GmbH)), mixed esters of pentaerythritol, fatty acids, citric acid and fatty alcohol according to DE 11 65 574 and/or mixed esters of fatty acids with 6 to 22 carbon atoms, methyl glucose and polyols, for example glycerol or polyglycerol, citric acid esters e.g. glyceryl stearate citrate, glyceryl oleate citrate and dilauryl citrate.

Anionic emulsifiers or surfactants can contain water-solubilizing anionic groups, e.g. a carboxylate, sulphate, sulphonate or phosphate group and a lipophilic residue. Skin-compatible anionic surfactants are known by a person skilled in the art in large numbers and are commercially available. These can be alkyl sulphates or alkyl phosphates in the form of their alkali, ammonium or alkanolammonium salts, alkyl ether sulphates, alkyl ether carboxylates, acyl sarcosinates and sulphosuccinates and acyl glutamates in the form of their alkali or ammonium salts.

Cationic emulsifiers and surfactants can also be added. As these, it is possible to use in particular quaternary ammonium compounds, especially those provided with at least one linear and/or branched, saturated or unsaturated alkyl chain with 8 to 22 carbon atoms, for instance alkyl trimethylammonium halides, e.g. cetyl trimethylammonium chloride or bromide or behenyl trimethylammonium chloride, as well as dialkyl dimethylammonium halides, e.g. distearyl dimethylammonium chloride.

Furthermore, monoalkylamido quats e.g. palmitamidopropyl-trimethylammonium chloride or corresponding dialkylamido quats can be used.

Furthermore, quaternary ester compounds with good biodegradability can be used, for instance quaternized fatty acid esters based on mono-, di- or triethanolamine. Furthermore, alkylguanidinium salts can also be added as cationic emulsifiers.

Typical examples of mild, i.e. especially skin-compatible surfactants are fatty alcohol-polyglycol ether sulphates, monoglyceride sulphates, mono- and/or dialkyl sulphosuccinates, fatty acid isethionates, fatty acid sarcosinates, fatty acid taurides, fatty acid glutamates, ether carboxylic acids, alkyl oligoglucosides, fatty acid glucamides, alkylamidobetaines and/or protein fatty acid condensates, the latter for example based on wheat proteins.

Furthermore, it is possible to use amphoteric surfactants, e.g. betaines, amphoacetates or amphopropionates, for example substances such as the N-alkyl-N,N-dimethylammonium glycinates, for example coconut alkyldimethylammonium glycinate, N-acylaminopropyl-N,N-dimethylammonium glycinates, for example coconut acylaminopropyldimethylammonium glycinate, and 2-alkyl-3-carboxylmethyl-3-hydroxyethylimidazolines with in each case 8 to 18 carbon atoms in the alkyl or acyl group and coconut acylaminoethylhydroxyethylcarboxymethyl glycinate.

Among the amphoteric surfactants, it is possible to use those surface active compounds which, apart from a $C_{8/18}$ alkyl or acyl group in the molecule, contain at least one free amino group and at least one —COOH— or —SO$_3$H— group and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropyl glycines, N-alkyltaurines, N-alkylsarcosines, 2-alkylaminopropionic acids and alkylaminoacetic acids with in each case about 8 to 18 carbon atoms in the alkyl group. Further examples of amphoteric surfactants are N-coconut alkylaminopropionate, coconut acylaminoethylaminopropionate and $C_{12/18}$-acyl sarcosine.

Suitable thickeners are for example polysaccharides, especially xanthan gum, guar-guar, agar-agar, alginates and tyloses, carboxymethylcellulose and hydroxyethylcellulose, also higher-molecular polyethylene glycol mono- and diesters of fatty acids, polyacrylates (e.g. Carbopole™ or Synthalene™), polyacrylamides, polyvinyl alcohol and polyvinylpyrrolidone, surfactants such as for example ethoxylated fatty acid glycerides, esters of fatty acids with polyols such as for example pentaerythritol or trimethylolpropane, fatty alcohol ethoxylates with narrower distribution of homologues or alkyl oligoglucosides and electrolytes such as common salt and ammonium chloride.

All thickening agents known by a person skilled in the art may come into consideration as thickeners for thickening oil phases. Waxes, such as hydrogenated castor wax, beeswax or microwax, should be mentioned in particular. Furthermore, it is also possible to use inorganic thickening agents, such as silica, alumina or sheet silicates (e.g. hectorite, Laponite, saponite). These inorganic oil phase thickeners can be hydrophobically modified. For thickening/stabilizing water-in-oil emulsions, it is possible in particular to use Aerosils, sheet silicates and/or metal salts of fatty acids, for example zinc stearate.

For example NaCl, low-molecular non-ionic surfactants, such as cocoamides DEA/MEA and laureth-3, or polymeric, high-molecular, associative, highly-ethoxylated fat derivatives, such as PEG-200 hydrogenated glyceryl palmate can be contained as viscosity controllers for aqueous surfactant systems.

As UV-light protection filters it is possible for example to use organic substances that are able to absorb ultraviolet rays and reemit the absorbed energy in the form of longer-wave radiation, e.g. heat. UVB filters can be oil-soluble or water-soluble. The following may be mentioned as examples of oil-soluble UVB-light protection filters: 3-benzylidene camphor and derivatives thereof, e.g. 3-(4-methylbenzylidene)camphor, 4-aminobenzoic acid derivatives, for example 4-(dimethylamino)benzoic acid-2-ethylhexyl ester, 4-(dimethylamino) benzoic acid-2-ethylhexyl ester and 4-(dimethylamino)-benzoic acid amyl ester, esters of cinnamic acid, for example 4-methoxycinnamic acid-2-ethylhexyl ester, 4-methoxycinnamic acid isopentyl ester, 2-cyano-3-phenyl-cinnamic acid-2-ethylhexyl ester(octocrylene), esters of salicylic acid, for example salicylic acid-2-ethylhexyl ester, salicylic acid-4-isopropylbenzyl ester, salicylic acid homomenthyl ester, derivatives of benzophenone, for example 2-hydroxy-4-methoxybenzophenone, 2-hydroxy-4-methoxy-4'-methyl-benzophenone, 2,2'-dihydroxy-4-methoxybenzophenone, esters of benzalmalonic acid, for example 4-methoxybenzalmalonic acid di-2-ethylhexyl ester, triazine derivatives, for example 2,4,6-trianilino-(p-carbo-2'-ethyl-1'-hexyloxy)-1,3,5-triazine and octyltriazone, propane-1,3-diones, for example 1-(4-tert.-butylphenyl)-3-(4'-methoxyphenyl) propane-1,3-dione.

The following are possible as water-soluble UVB-light protection filters: 2-phenylbenzimidazole-5-sulphonic acid and alkali-metal, alkaline-earth, ammonium, alkylammonium, alkanolammonium and glucammonium salts thereof, sulphonic acid derivatives of benzophenone, for example 2-hydroxy-4-methoxybenzophenone-5-sulphonic acid and salts thereof, sulphonic acid derivatives of 3-benzylidenecamphor, for example 4-(2-oxo-3-bornylidenemethyl)benzenesulphonic acid and 2-methyl-5-(2-oxo-3-bornylidene) sulphonic acid and salts thereof.

Derivatives of benzoylmethane in particular may come into consideration as typical UVA-light protection filters, for example 1-(4'-tert.-butylphenyl)-3-(4'-methoxyphenyl)propane-1,3-dione or 1-phenyl-3-(4'-isopropylphenyl)propane-1,3-dione. The UV-A and UV-B filters can of course also be used in mixtures.

In addition to the aforementioned soluble substances, for this purpose consideration may also be given to insoluble pigments, namely finely divided metal oxides or salts, for example titanium dioxide, zinc oxide, iron oxide, aluminium oxide, cerium oxide, zirconium oxide, silicates (talc), barium sulphate and zinc stearate. The particles should have an average diameter of less than 100 nm, e.g. between 5 and 50 nm and especially between 15 and 30 nm. They can have a spherical shape, but it is also possible to use particles that have an ellipsoidal shape or deviate in some other way from spherical. A relatively new class of light protection filters are micronized organic pigments, for example 2,2'-methylene-bis-{6-(2H-benzotriazol-2-yl)-4-(1,1,3,3-tetramethylbutyl) phenol} with a particle size of <200 nm, which can be obtained e.g. as 50% aqueous dispersion.

Further suitable UV-light protection filters can be found in the review by P. Finkel in SÖFW-Journal 122, 543 (1996). In addition to the two aforementioned groups of primary UV-light protection filters, it is also possible to use secondary sunscreen agents of the antioxidant type, which interrupt the photochemical reaction chain that is triggered when UV radiation penetrates into the skin.

Antioxidants and vitamins that can be used are e.g. superoxide dismutase, tocopherol (vitamin E), tocopherol sorbate, tocopherol acetate, other esters of tocopherol, dibutylhydroxytoluene and ascorbic acid (vitamin C) and their salts as well as derivatives thereof (e.g. magnesium ascorbyl phosphate, sodium ascorbyl phosphate, ascorbyl sorbate), ascorbyl esters of fatty acids, butylated hydroxybenzoic acid and salts thereof, peroxides e.g. hydrogen peroxide, perborates, thioglycolates, persulphate salts, 6-hydroxy-2,5,7,8-tetramethylchroman-2-carboxylic acid (TROLOX®), gallic acid and alkyl esters thereof, uric acid and salts and alkyl esters thereof, sorbic acid and salts thereof, lipoic acid, ferulic acid, amines (e.g. N,N-diethylhydroxylamine, amino-guanidines), sulphydryl compounds (e.g. glutathione), dihydroxyfumaric acid and salts thereof, glycine pidolate, arginine pilolate, nordihydroguaiaretic acid, bioflavonoids, curcumin, lysine, L-methionine, proline, superoxide dismutase, silymarin, tea extract, grapefruit peel/kernel extract, melanin, rosemary extract, thioctic acid, resveratrol, oxyresveratrol, etc.

Ethanol, isopropyl alcohol or polyols for example can be used as hydrotropes for improving the flow behaviour and application properties. Polyols that may be considered here can have 2 to 15 carbon atoms and at least two hydroxyl groups. Typical examples comprise: glycerol alkylene glycols, for example ethylene glycol, diethylene glycol, propylene glycol, butylene glycol, hexylene glycol and polyethylene glycols with an average molecular weight from 100 to 1000 dalton, technical oligoglycerol mixtures with an intrinsic degree of condensation from 1.5 to 10 such as technical diglycerol mixtures with a diglycerol content from 40 to 50 wt %, methylol compounds, such as in particular trimethylolethane, trimethylolpropane, trimethylolbutane, pentaerythritol and dipentaerythritol, lower alkyl glucosides, especially those with 1 to 4 carbon atoms in the alkyl residue, for example methyl and butyl glucosides, sugar alcohols with 5 to 12 carbon atoms, for example sorbitol or mannitol, sugars with 5 to 12 carbon atoms, for example glucose or sucrose, amino sugars, for example glucamine Solids that can be used are for example iron oxide pigments, titanium dioxide or zinc oxide particles and those additionally mentioned under "UV screening agents". Furthermore, it is also possible to use particles that produce special sensory effects, such as nylon-12, boron nitride, polymer particles such as polyacrylate or polymethylacrylate particles or silicone elastomers. Fillers that can be used include starch and starch derivatives, such as tapioca starch, distarch phosphate, aluminium or sodium starch, octenyl succinate and pigments that have neither mainly UV filtering nor colouring action, for example Aerosile® (CAS No. 7631-86-9).

As film formers, e.g. for improving water resistance, it is possible for example to use: polyurethanes, dimethicones, copolyols, polyacrylates or PVP/VA copolymer (PVP=polyvinylpyrrolidone, VA=vinyl acetate). The following for example can be used as fat-soluble film formers: polymers based on polyvinylpyrrolidone (PVP), polyvinylpyrrolidone copolymers, PVP/hexadecene copolymer or PVP/eicosene copolymer.

Glycol distearates or PEG-3 distearate for example can be used as nacreous additives.

Suitable deodorant active substances are for example odour masking agents such as the usual perfume constituents, odour absorbers, for example the sheet silicates described in the patent Offenlegungsschrift [publication of unexamined application] DE 40 09 347, of these in particular montmorillonite, kaolinite, ilite, beidelite, nontronite, saponite, ilectorite, bentonite, smectite, in addition for example zinc salts of ricinoleic acid. Germination inhibitors are also suitable to be incorporated. Germination-inhibiting substances are for example 2,4,4'-trichloro-2'-hydroxydiphenyl ether (Irgasan), 1,6-di-(4-chlorophenylbiguanido)-hexane(chlorhexidine), 3,4,4'-trichlorocarbonilide, quaternary ammonium compounds, clove oil, mint oil, thyme oil, triethylcitrate, farnesol (3,7,11-trimethyl-2,6,10-dodecatrien-1-ol), ethylhexyl glyceryl ether, polyglyceryl-3 caprylate (TEGO® Cosmo P813, Evonik Goldschmidt GmbH), and the active agents described in the unexamined patent applications DE 198 55 934, DE 37 40 186, DE 39 38 140, DE 42 04 321, DE 42 29 707, DE 42 29 737, DE 42 38 081, DE 43 09 372, DE 43 24 219 and EP 666 732.

Astringents, for example basic aluminium chlorides such as aluminium chlorohydrate ("ACH") and zirconium-aluminium-glycine salts ("ZAG"), can be used as antiperspirant active substances.

N,N-Diethyl-m-toluamide, 1,2-pentanediol or Insect Repellent 3535 for example can be used as insect repellents.

Dihydroxyacetone and erythrulose for example can be used as self-tanning agents.

Mixtures of individual or several alkylparaben esters with phenoxyethanol for example can be used as preservatives. The alkylparaben esters can be methylparaben, ethylparaben, propylparaben and/or butylparaben. Other alcohols, for example benzyl alcohol or ethanol, can also be used instead of phenoxyethanol. Furthermore, other usual preservatives can also be used, such as sorbic or benzoic acid, salicylic acid, 2-bromo-2-nitropropane-1,3-diol, chloroacetamide, diazolidinyl urea, DMDM hydantoin, iodopropynyl butylcarbamate, sodium hydroxymethyl glycinate, methyl isothiazoline, chloromethyl isothiazoline, ethylhexyl glycerol or caprylyl glycol.

For example organic quaternary compounds such as cetrimonium chloride, dicetyldimonium chloride, behentrimonium chloride, distearyldimonium chloride, behentrimonium methosulphate, distearoylethyldimonium chloride, palmitamidopropyltrimonium chloride, guar hydroxypropyltrimonium chloride, hydroxypropylguar hydroxypropyltrimonium chloride, or quaternium-80 or also amine derivatives e.g. aminopropyldimethicones or stearamidopropyl dimethylamines can be used as conditioners.

Natural or synthetic fragrances or mixtures thereof can be used as perfumes. Natural fragrances are extracts of flowers (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (mace, angelica, celery, cardamom, costus, iris, thyme), needles and branches (spruce, fir, pine, mountain pine), resins and balsams (galbanum, elemi, benzoin, myrrh, olibanum, opoponax). Furthermore, animal raw materials may come into consideration, for example civet and castoreum. Typical synthetic fragrance compounds are products of the type of the esters, ethers, aldehydes, ketones, alcohols and hydrocarbons. Fragrance compounds of the ester type are e.g. benzyl acetate, phenoxyethyl isobutyrate, p-tert.-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include for example benzylethyl ether, the aldehydes include e.g. the linear alkanals with 8 to 18 carbon atoms, citral, citronellal, citronellyloxy acetaldehyde, cyclamen aldehyde, hydroxycitronellal, lilial and bourgeonal, the ketones include e.g. the ionones, α-isomethylionone and methyl-cedryl ketone, the alcohols include anethole, citronellol, eugenol, isoeugenol, geraniol, linalool, phenylethyl alcohol and terpineol, the hydrocarbons include mainly the terpenes and balsams. Mixtures of various fragrances can be used, which together produce an attractive perfume note. Essential oils of low volatility, which are generally used as flavour components, are also suitable as perfumes, e.g. sage oil, chamomile oil, clove oil, melissa oil, mint oil, cinnamon leaf oil, lime blossom oil, juniper berry oil, vetiver oil, olibanum oil, galbanum oil, labolanum oil and lavandin oil. Bergamot oil, dihydromyrcenol, lilial, lyral, citronellol, phenylethyl alcohol, α-hexyl cinnamaldehyde, geraniol, benzylacetone, cyclamen aldehyde, linalool, Boisambrene Forte, Ambroxan, indole, hedione, sandelice, lemon oil, mandarin orange oil, orange oil, allylamyl glycolate, cylovertal, lavandin oil, clary sage oil, β-damascone, geranium oil bourbon, cyclohexyl salicylate, vertofix coeur, iso-E-super, Fixolide NP, evernyl, iraldein gamma, phenylacetic acid, geranyl acetate, benzyl acetate, rose oxide, romillate, irotyl and floramat can be used, alone or in mixtures.

Dyes that can be used are the substances that are suitable and permitted for cosmetic purposes, as listed for example in the publication "Kosmetische Färbemittel" [Cosmetic colourants] of the Dye Commission of the Deutsche Forschungsgemeinschaft [German Research Association], Verlag Chemie, Weinheim, 1984, p. 81 to 106. These dyes are usually used in concentrations from 0.001 to 0.1 wt %, relative to the total mixture.

Biogenic active substances are for example tocopherol, tocopherol acetate, tocopherol palmitate, ascorbic acid, polyphenols, deoxyribonucleic acid, coenzyme Q10, retinol, AHA acids, amino acids, hyaluronic acid, alpha-hydroxy acids, isoflavones, polyglutamic acid, creatine (and creatine derivatives), guanidine (and guanidine derivatives), pseudoceramides, essential oils, peptides, protein hydrolysates, plant extracts, bisabolol, allantoin, panthenol, phytantriol, idebenone, liquorice extract, glycyrrhicidine and idebenone, scleroglucan, β-glucan, santalbin acid and vitamin complexes. Examples of plant extracts are chestnut extract, chamomile extract, rosemary extract, blackcurrant and redcurrant extract, birch extract, rose hip extract, algae extracts, green tea extract, aloe extract, ginseng extract, ginkgo extract, grapefruit extract, calendula extract, camphor, thyme extract, mangosteen extract, cystus extract, *Terminalia arjuna* extract, oats extract, oregano extract, raspberry extract, strawberry extract, etc.

The biogenic active substances can also include the so-called barrier lipids, for which we may mention for example ceramides, phytosphingosine and derivatives, sphingosine and derivatives, sphinganine and derivatives, pseudoceramides, phospholipids, lysophospholipids, cholesterol and derivatives, cholesteryl esters, free fatty acids, lanolin and derivatives, squalane, squalene and related substances.

The biogenic active substances also include, in the sense of the invention, anti-acne agents, e.g. benzyl peroxide, phytosphingosine and derivatives, nicotinamide hydroxybenzoate, nicotinaldehyde, retinoic acid and derivatives, salicylic acid and derivatives, citronellic acid etc. and anticellulite agents e.g. xanthine compounds such as caffeine, theophylline, theobromine and aminophylline, carnitine, carnosine, salicyloyl phytosphingosine, phytosphingosines, santalbin acid etc., as well as antidandruff agents, for example salicylic acid and derivatives, zinc pyrithione, selenium sulphide, sulphur, cyclopiroxolamine, bifonazole, climbazole, octopirox and actirox etc., as well as astringents e.g. alcohol, aluminium derivatives, gallic acid, pyridoxine salicylate, zinc salts e.g. zinc sulphate, acetate, chloride, lactate, zirconium hydrochlorides etc. Bleaching agents such as kojic acid, arbutin, vitamin C and derivatives, hydroquinone, turmeric oil, creatinine, sphingolipids, nicotinamide, etc. can also be included among the biogenic active substances.

For example ethoxylated glycerol fatty acid esters, for example PEG-7 glycerol cocoate, or cationic polymers, for example polyquaternium-7 or polyglycerol esters can be contained as care additives.

As overfatting agents it is possible to use substances such as for example lanolin and lecithin and polyethoxylated or acylated lanolin and lecithin derivatives, polyol fatty acid esters, monoglycerides and fatty acid alkanolamides, wherein the latter serve simultaneously as foam stabilizers.

For example aliphatic alcohols such as ethanol, propanol or 1,3-propanediol, cyclic carbonates such as ethylene carbonate, propylene carbonate, glycerol carbonate, esters of mono- or polycarboxylic acids such as ethyl acetate, ethyl lactate, dimethyl adipate and diethyl adipate, propylene glycol, dipropylene glycol, glycerol, glycerol carbonate or water can be used as solvents.

The care formulations according to the invention preferably have, as additional components, barrier lipids selected from the group containing ceramides, cholesterol, fatty acids.

Moreover, it is preferable for the care formulations according to the invention to contain, as additional components, lipid modulators, for example linolenic acid, conjugated linoleic acid, gamma linolenic acid, phytosphingosine, salicyloyl phytosphingosine, short-chain and medium-chain ceramides ($C_1$-$C_{10}$), uronic acid, cholesterol sulphate, phytosterols, vitamin D, leukotrienes, farnesol, 15-deoxyprostaglandin J2, 9-hydroxyoctadecadienoic acid (9-HODE), preferably lipid modulators selected from the group containing creatine, nicotinamide, retinol, arjunolic acid.

Care formulations according to the invention can be used as skin care, facial care, head care, body care, intimate care, foot care, hair care, nail care, dental hygiene, lip care or oral hygiene products. Examples of hair care products are hair detergents, hair treatments, hair rinses, hair fluid, hair gel, hair tonic, hair wax, hair lacquer, hair spray, hair cream, hair mousse, hair balm, antidandruff shampoo. Examples of body care products are shower gel, cream bath, cream gel, shower oil, shower gel, washing gel, wash-peeling, cleansing lotion, face mask, face lotion, facial peeling, eye cream, night cream, cleansing mask, lotion pads, cleansing wipes, cleansing lotion, cleansing milk, cleansing gel, aftershave gel, aftershave balm, tanning milk, after-sun products, self-tanning agents, foot lotion, foot spray, body lotion, body gel, body spray, body milk, body peeling, body oil, body butter.

Examples of lip care products are lip balm, lip cream, lip-care sticks.

Care formulations according to the invention can be used in the form of an emulsion such as oil-in-water (O/W), water-in-oil (W/O) or water-in-silicone (W/S) emulsions, multiple emulsions such as W/O/W and O/W/O emulsions, also called hydrodispersions or lipodispersions, a suspension, a solution, a cream, an ointment, a paste, a gel, an aerosol, a spray, a cleaning product, a makeup or sunscreen preparation or a face lotion or a stick, e.g. fat stick or water-containing stick.

The yeast extract produced according to the invention can also be used as food supplement for animals and/or humans. Said extract can be administered with the food.

A dermatologically active agent or a food supplement must contain a specified minimum amount of protein in the yeast extract. In a preferred embodiment the yeast extract contains in increasing order of preference at least 0.5, 1, 2.5, 5, 10 or 25 mg protein/mL or is in the range from 0.05 to 100, 0.1 to 80, 0.5 to 50 or 1 to 25 mg protein/mL.

The yeast extract produced according to the invention can be used in cosmetic treatments of the hair and/or skin. In a preferred embodiment the term "skin and/or hair", as used herein, means any part of the human or animal body that is accessible for external use of a dermatological agent. In a preferred embodiment the term "cosmetic treatment", as used herein, means the improvement of nonpathological manifestations, which in particular only improves the aesthetic impression. With a treatment of this kind it is possible for example to achieve skin firming, improved humidity of the skin, an even skin tone, or improvement of perspiration.

The inventors found, surprisingly, that the treatment of skin cells with the yeast extract produced according to the invention is suitable for treating diseases.

The present invention is further illustrated with the following figures and nonlimiting examples, from which further features, embodiments, aspects and advantages of the present invention can be seen.

EXAMPLE 1

Growth of Various Yeast Strains Under Stress by Exposure to Medium with Low pH

In order to investigate whether it is possible to stress yeast strains by exposure to medium with low pH, and to investigate which yeast strains possibly display suitable or advantageous growth properties at low pH, the growth of one representative from each of three genera, namely *Saccharomyces*, *Pichia* and *Yarrowia*, was investigated at pH=2.

A preculture of the respective yeast strain to be investigated is cultured overnight in standard medium (per litre: 33 g glucose monohydrate, 0.88 g magnesium sulphate×7H$_2$O, 0.2 g calcium chloride×2H$_2$O, 4.83 ammonium chloride, 0.06 g sodium chloride, 1 g potassium dihydrogen phosphate, 0.059 g myo-inositol, 20 g MOPS, 0.3 mL trace element solution (per kg: 100 g 8M H$_2$SO$_4$, 50 g of citric acid monohydrate, 48 g FeSO$_4$×7H$_2$O, 16.7 g ZnSO$_4$×7H$_2$O, 2.5 g CuSO$_4$×5H$_2$O, 1.88 g MnSO$_4$×H$_2$O, 2 g H$_3$BO$_3$, 2 g NaMoO$_4$×2H$_2$O, 0.5 g KI) and 0.3 mL vitamin solution (per litre: 5 g nicotinic acid, 5 g calcium-D-pantothenic acid, 5 g thiamine, 3.33 p-aminobenzoate, 0.5 g pyridoxine, 0.0167 biotin), the pH of which was adjusted to 2 with sulphuric acid. The optical density is monitored continuously by spectrophotometry.

Figure 1:
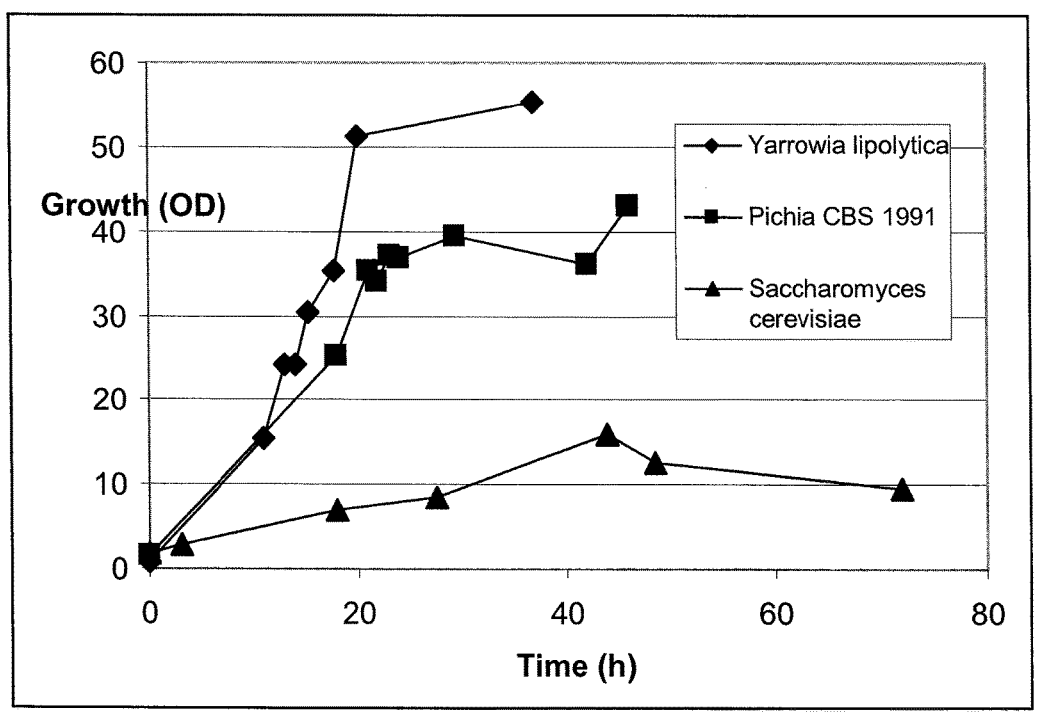
FIG. 1 shows the growth of yeast cells of the genera *Yarrowia*, *Pichia* and *Saccharomyces* over time at pH 2.

The results of the test are shown in FIG. 1. It can be seen that all the strains used show detectable growth in these conditions, but the representative of the genus *Yarrowia* at pH=2 under the same conditions shows faster growth than the comparative genera, and also reaches a higher optical density.

EXAMPLE 2

Comparative Characterization of the Action of Yeast Cells that were Stressed Either by Increased Temperature, Treatment with Hydrogen Peroxide or Exposure to Medium with Low pH, Using Chip Arrays, on Human Fibroblasts It was investigated whether stress by exposure to medium with low pH exerts the same effect on yeast cells as stress through increased temperature or treatment with hydrogen peroxide and whether differently stressed yeast cells or their extracts differ. Saccharomyces cerevisiae was selected as the model organism.

Production of the Yeast Extract

The preculture is set up as described above and adjusted to a pH of 5.4. The medium is inoculated in the shaking flask without baffles with addition of antifoaming agent. The temperature is 30° C. and the speed is 180 rpm (amplitude: 2.5 cm). The optical density is determined beforehand, it is measured continuously, and at OD>35 the respective stress situation is created, i.e. by increasing the temperature to 37° C., by adding sulphuric acid up to the desired pH or by adding hydrogen peroxide.

Then the cells are harvested by centrifugation and frozen or lysed by aqueous lysis. For this, the extract is suspended and treated by means of a high-pressure homogenizer. The suspension is filtered off or centrifuged and the aqueous solution is taken as the end product.

Test Principle and Execution of the Experiments with Chip Arrays:

In these tests, the effect of yeast extract on the behaviour of human dermal fibroblasts is investigated, which are a recognized model for human skin. For this purpose, after the extract treatment the cells are lysed, their RNA is isolated, and the DNA obtained by reverse transcription is investigated by means of a chip for regulation of the expression of dermatologically relevant markers. Markers whose upregulation or downregulation indicates a positive effect on the morphology and physiology of the skin, especially markers of the Wnt-pathway and of the ECM, are used exclusively. The Wnt genes code for a large family of secreted proteins.

To date, 19 Wnt proteins have been identified in humans. Both the various subgroups of the Wnts in individual species, and Wnts in comparison between different species sometimes show very large homologies. In humans, for example, the individual Wnt proteins show agreement from 27 to 83% (Miller, 2001). The central molecule of the canonical Wnt signal cascade is β-catenin (βCat), whose stability is regulated by the Wnt proteins. Investigations of embryonic and postnatal skin have shown that Wnt proteins play an essential role in hair follicle development. In particular, the proteins Wnt10a, Wnt10b and Wnt5a are specifically expressed in early stages of hair follicle development (Reddy et al., 2001).

Most of the known communication mechanisms are found in the skin. By the Wnt-pathway, basal cells keep the stem cell character preferentially. As cells age, there is accumulation of cellular and molecular damage, causing reduced regenerative capacity of tissues and organs. This reduced regenerative capacity is partly influenced by the change in self-renewal capacity and differentiation potential of tissue-specific adult stem cells from the fat tissue. It is known that the WNT signal pathway, a known signal pathway that regulates the self-renewal potential and the differentiation potential of many stem cells, therefore has an effect on the growth of stem cells. In addition, with Wnt and β-catenin expression, epidermal proliferation, differentiation and migration is increased and therefore wound healing is accelerated.

The physical properties of the connective tissue and the associated skin-firming are determined inter alia by the extracellular matrix, so that the cells are influenced in their differentiation, migration and proliferation. The matrix is formed by the cells located within it (fibroblasts, myofibroblasts, lipoblasts, osteoblasts and chondroblasts). The extracellular matrix is made up of macromolecules, which consist of glycosaminoglycans and fibrous proteins. Interaction of the lymphatic system, of the extracellular matrix and excessive fat-accumulation are involved in skin-firming. The total body fat is determined by the equilibrium between de-novo differentiation, growth and apoptosis (autolysis) of the adipocytes. Adipocyte differentiation is a complex process, which begins at birth and continues throughout life.

A complete list of the markers used is shown in Table 1.

TABLE 1

List of the markers taken into account for the chip experiments:

| Gene ID | Gene symbol | Description of the gene | Chromosome |
|---|---|---|---|
| 9 | NAT1 | N-acetyltransferase 1 (arylamine N-acetyltransferase) | 8p23.1-p21.3 |
| 10 | NAT2 | N-acetyltransferase 2 (arylamine N-acetyltransferase) | 8p22 |
| 30 | ACAA1 | acetyl-Coenzyme A acyltransferase 1 | 3p23-p22 |
| 33 | ACADL | acyl-Coenzyme A dehydrogenase, long chain | 2q34-q35 |
| 34 | ACADM | acyl-Coenzyme A dehydrogenase, C-4 to C-12 straight chain | 1p31 |
| 51 | ACOX1 | acyl-Coenzyme A oxidase 1, palmitoyl | 17q24-q25 |
| 90 | ACVR1 | activin A receptor, type I | 2q23-q24 |
| 91 | ACVR1B | activin A receptor, type IB | 12q13 |
| 92 | ACVR2A | activin A receptor, type IIA | 2q22.3 |
| 93 | ACVR2B | activin A receptor, type IIB | 3p22 |
| 94 | ACVRL1 | activin A receptor type II-like 1 | 12q11-q14 |
| 154 | ADRB2 | adrenergic, beta-2-, receptor, surface | 5q31-q32 |
| 176 | ACAN | aggrecan | 15q26.1 |
| 268 | AMH | anti-Mullerian hormone | 19p13.3 |
| 269 | AMHR2 | anti-Mullerian hormone receptor, type II | 12q13 |
| 324 | APC | adenomatous polyposis coli | 5q21-q22 |
| 325 | APCS | amyloid P component, serum | 1q21-q23 |
| 335 | APOA1 | apolipoprotein A-I | 11q23-q24 |
| 336 | APOA2 | apolipoprotein A-II | 1q21-q23 |

TABLE 1-continued

List of the markers taken into account for the chip experiments:

| Gene ID | Gene symbol | Description of the gene | Chromosome |
| --- | --- | --- | --- |
| 345 | APOC3 | apolipoprotein C-III | 11q23.1-q23.2 |
| 364 | AQP7 | aquaporin 7 | 9p13 |
| 387 | RHOA | ras homolog gene family, member A | 3p21.3 |
| 595 | CCND1 | cyclin D1 | 11q13 |
| 633 | BGN | biglycan | Xq28 |
| 650 | BMP2 | bone morphogenetic protein 2 | 20p12 |
| 652 | BMP4 | bone morphogenetic protein 4 | 14q22-q23 |
| 653 | BMP5 | bone morphogenetic protein 5 | 6p12.1 |
| 654 | BMP6 | bone morphogenetic protein 6 | 6p24-p23 |
| 655 | BMP7 | bone morphogenetic protein 7 | 20q13 |
| 656 | BMP8B | bone morphogenetic protein 8b | 1p35-p32 |
| 657 | BMPR1A | bone morphogenetic protein receptor, type IA | 10q22.3 |
| 658 | BMPR1B | bone morphogenetic protein receptor, type IB | 4q22-q24 |
| 659 | BMPR2 | bone morphogenetic protein receptor, type II (serine/threonine kinase) | 2q33-q34 |
| 815 | CAMK2A | calcium/calmodulin-dependent protein kinase II alpha | 5q33.1 |
| 816 | CAMK2B | calcium/calmodulin-dependent protein kinase II beta | 22q12 |
| 817 | CAMK2D | calcium/calmodulin-dependent protein kinase II delta | 4q26 |
| 818 | CAMK2G | calcium/calmodulin-dependent protein kinase II gamma | 10q22 |
| 894 | CCND2 | cyclin D2 | 12p13 |
| 896 | CCND3 | cyclin D3 | 6p21 |
| 948 | CD36 | CD36 molecule (thrombospondin receptor) | 7q11.2 |
| 960 | CD44 | CD44 molecule (Indian blood group) | 11p13 |
| 961 | CD47 | CD47 molecule | 3q13.1-q13.2 |
| 1030 | CDKN2B | cyclin-dependent kinase inhibitor 2B (p15, inhibits CDK4) | 9p21 |
| 1101 | CHAD | chondroadherin | 17q21.33 |
| 1277 | COL1A1 | collagen, type I, alpha 1 | 17q21.33 |
| 1278 | COL1A2 | collagen, type I, alpha 2 | 7q22.1 |
| 1280 | COL2A1 | collagen, type II, alpha 1 | 12q13.11 |
| 1281 | COL3A1 | collagen, type III, alpha 1 | 2q31 |
| 1282 | COL4A1 | collagen, type IV, alpha 1 | 13q34 |
| 1284 | COL4A2 | collagen, type IV, alpha 2 | 13q34 |
| 1286 | COL4A4 | collagen, type IV, alpha 4 | 2q35-q37 |
| 1288 | COL4A6 | collagen, type IV, alpha 6 | Xq22 |
| 1289 | COL5A1 | collagen, type V, alpha 1 | 9q34.2-q34.3 |
| 1290 | COL5A2 | collagen, type V, alpha 2 | 2q14-q32 |
| 1291 | COL6A1 | collagen, type VI, alpha 1 | 21q22.3 |
| 1292 | COL6A2 | collagen, type VI, alpha 2 | 21q22.3 |
| 1293 | COL6A3 | collagen, type VI, alpha 3 | 2q37 |
| 1301 | COL11A1 | collagen, type XI, alpha 1 | 1p21 |
| 1311 | COMP | cartilage oligomeric matrix protein | 19p13.1 |
| 1374 | CPT1A | carnitine palmitoyltransferase 1A (liver) | 11q13.1-q13.2 |
| 1375 | CPT1B | carnitine palmitoyltransferase 1B (muscle) | 22q13.33 |
| 1376 | CPT2 | carnitine palmitoyltransferase II | 1p32 |
| 1387 | CREBBP | CREB binding protein | 16p13.3 |
| 1452 | CSNK1A1 | casein kinase 1, alpha 1 | 5q32 |
| 1454 | CSNK1E | casein kinase 1, epsilon | 22q13.1 |
| 1457 | CSNK2A1 | casein kinase 2, alpha 1 polypeptide | 20p13 |
| 1459 | CSNK2A2 | casein kinase 2, alpha prime polypeptide | 16q21 |
| 1460 | CSNK2B | casein kinase 2, beta polypeptide | 6p21-p12 |
| 1462 | VCAN | versican | 5q14.3 |
| 1474 | CST6 | cystatin E/M | 11q13 |
| 1487 | CTBP1 | C-terminal binding protein 1 | 4p16 |
| 1488 | CTBP2 | C-terminal binding protein 2 | 10q26.13 |
| 1499 | CTNNB1 | catenin (cadherin-associated protein), beta 1, 88 kDa | 3p21 |
| 1509 | CTSD | cathepsin D | 11p15.5 |
| 1512 | CTSH | cathepsin H | 15q24-q25 |
| 1520 | CTSS | cathepsin S | 1q21 |
| 1522 | CTSZ | cathepsin Z | 20q13 |
| 1544 | CYP1A2 | cytochrome P450, family 1, subfamily A, polypeptide 2 | 15q24.1 |
| 1548 | CYP2A6 | cytochrome P450, family 2, subfamily A, polypeptide 6 | 19q13.2 |
| 1549 | CYP2A7 | cytochrome P450, family 2, subfamily A, polypeptide 7 | 19q13.2 |
| 1553 | CYP2A13 | cytochrome P450, family 2, subfamily A, polypeptide 13 | 19q13.2 |
| 1579 | CYP4A11 | cytochrome P450, family 4, subfamily A, polypeptide 11 | 1p33 |

TABLE 1-continued

List of the markers taken into account for the chip experiments:

| Gene ID | Gene symbol | Description of the gene | Chromosome |
|---|---|---|---|
| 1581 | CYP7A1 | cytochrome P450, family 7, subfamily A, polypeptide 1 | 8q11-q12 |
| 1582 | CYP8B1 | cytochrome P450, family 8, subfamily B, polypeptide 1 | 3p22-p21.3 |
| 1593 | CYP27A1 | cytochrome P450, family 27, subfamily A, polypeptide 1 | 2q33-qter |
| 1605 | DAG1 | dystroglycan 1 (dystrophin-associated glycoprotein 1) | 3p21 |
| 1622 | DBI | diazepam binding inhibitor (GABA receptor modulator, acyl-Coenzyme A binding protein) | 2q12-q21 |
| 1634 | DCN | decorin | 12q21.33 |
| 1634 | DCN | decorin | 12q21.33 |
| 1805 | DPT | dermatopontin | 1q12-q23 |
| 1855 | DVL1 | dishevelled, dsh homolog 1 (Drosophila) | 1p36 |
| 1856 | DVL2 | dishevelled, dsh homolog 2 (Drosophila) | 17p13.2 |
| 1857 | DVL3 | dishevelled, dsh homolog 3 (Drosophila) | 3q27 |
| 1874 | E2F4 | E2F transcription factor 4, p107/p130-binding | 16q21-q22 |
| 1875 | E2F5 | E2F transcription factor 5, p130-binding | 8q21.2 |
| 1962 | EHHADH | enoyl-Coenzyme A, hydratase/3-hydroxyacyl Coenzyme A dehydrogenase | 3q26.3-q28 |
| 2006 | ELN | elastin | 7q11.23 |
| 2033 | EP300 | E1A binding protein p300 | 22q13.2 |
| 2033 | EP300 | E1A binding protein p300 | 22q13.2 |
| 2131 | EXT1 | exostoses (multiple) 1 | 8q24.11-q24.13 |
| 2132 | EXT2 | exostoses (multiple) 2 | 11p12-p11 |
| 2134 | EXTL1 | exostoses (multiple)-like 1 | 1p36.1 |
| 2135 | EXTL2 | exostoses (multiple)-like 2 | 1p21 |
| 2137 | EXTL3 | exostoses (multiple)-like 3 | 8p21 |
| 2167 | FABP4 | fatty acid binding protein 4, adipocyte | 8q21 |
| 2168 | FABP1 | fatty acid binding protein 1, liver | 2p11 |
| 2169 | FABP2 | fatty acid binding protein 2, intestinal | 4q28-q31 |
| 2170 | FABP3 | fatty acid binding protein 3, muscle and heart (mammary-derived growth inhibitor) | 1p33-p32 |
| 2171 | FABP5 | fatty acid binding protein 5 (psoriasisassociated) | 8q21.13 |
| 2172 | FABP6 | fatty acid binding protein 6, ileal | 5q33.3-q34 |
| 2173 | FABP7 | fatty acid binding protein 7, brain | 6q22-q23 |
| 2180 | ACSL1 | acyl-CoA synthetase long-chain family member 1 | 4q34-q35 |
| 2181 | ACSL3 | acyl-CoA synthetase long-chain family member 3 | 2q34-q35 |
| 2182 | ACSL4 | acyl-CoA synthetase long-chain family member 4 | Xq22.3-q23 |
| 2331 | FMOD | fibromodulin | 1q32 |
| 2335 | FN1 | fibronectin 1 | 2q34 |
| 2530 | FUT8 | fucosyltransferase 8 (alpha (1,6) fucosyltransferase) | 14q24.3 |
| 2535 | FZD2 | frizzled homolog 2 (Drosophila) | 17q21.1 |
| 2683 | B4GALT1 | UDP-Gal:betaGlcNAc beta 1,4-galactosyltransferase, polypeptide 1 | 9p13 |
| 2710 | GK | glycerol kinase | Xp21.3 |
| 2712 | GK2 | glycerol kinase 2 | 4q13 |
| 2713 | GK3P | glycerol kinase 3 pseudogene | 4q32.1 |
| 2811 | GP1BA | glycoprotein Ib (platelet), alpha polypeptide | 17pter-p12 |
| 2812 | GP1BB | glycoprotein Ib (platelet), beta polypeptide | 22q11.21q11.23 |
| 2814 | GP5 | glycoprotein V (platelet) | 3q29 |
| 2815 | GP9 | glycoprotein IX (platelet) | 3q21.3 |
| 2817 | GPC1 | glypican 1 | 2q35-q37 |
| 2932 | GSK3B | glycogen synthase kinase 3 beta | 3q13.3 |
| 3026 | HABP2 | hyaluronan binding protein 2 | 10q25.3 |
| 3036 | HAS1 | hyaluronan synthase 1 | 19q13.4 |
| 3037 | HAS2 | hyaluronan synthase 2 | 8q24.12 |
| 3038 | HAS3 | hyaluronan synthase 3 | 16q22.1 |
| 3158 | HMGCS2 | 3-hydroxy-3-methylglutaryl-Coenzyme A synthase 2 (mitochondrial) | 1p13-p12 |
| 3161 | HMMR | hyaluronan-mediated motility receptor (RHAMM) | 5q33.2-qter |
| 3339 | HSPG2 | heparan sulfate proteoglycan 2 | 1p36.1-p34 |
| 3339 | HSPG2 | heparan sulfate proteoglycan 2 | 1p36.1-p34 |
| 3340 | NDST1 | N-deacetylase/N-sulfotransferase (heparan glucosaminyl) 1 | 5q33.1 |
| 3371 | TNC | tenascin C | 9q33 |
| 3381 | IBSP | integrin-binding sialoprotein | 4q21-q25 |
| 3383 | ICAM1 | intercellular adhesion molecule 1 | 19p13.3-p13.2 |
| 3397 | ID1 | inhibitor of DNA binding 1, dominant negative helix-loop-helix protein | 20q11 |
| 3398 | ID2 | inhibitor of DNA binding 2, dominant negative helix-loop-helix protein | 2p25 |
| 3399 | ID3 | inhibitor of DNA binding 3, dominant negative helix-loop-helix protein | 1p36.13-p36.12 |

TABLE 1-continued

List of the markers taken into account for the chip experiments:

| Gene ID | Gene symbol | Description of the gene | Chromosome |
|---|---|---|---|
| 3400 | ID4 | inhibitor of DNA binding 4, dominant negative helix-loop-helix protein | 6p22-p21 |
| 3458 | IFNG | interferon, gamma | 12q14 |
| 3569 | IL6 | interleukin 6 (interferon, beta 2) | 7p21 |
| 3611 | ILK | integrin-linked kinase | 11p15.5-p15.4 |
| 3624 | INHBA | inhibin, beta A | 7p15-p13 |
| 3625 | INHBB | inhibin, beta B | 2cen-q13 |
| 3626 | INHBC | inhibin, beta C | 12q13.1 |
| 3655 | ITGA6 | integrin, alpha 6 | 2q31.1 |
| 3672 | ITGA1 | integrin, alpha 1 | 5q11.2 |
| 3673 | ITGA2 | integrin, alpha 2 (CD49B, alpha 2 subunit of VLA-2 receptor) | 5q23-q31 |
| 3674 | ITGA2B | integrin, alpha 2b (platelet glycoprotein IIb of IIb/IIIa complex, antigen CD41) | 17q21.32 |
| 3675 | ITGA3 | integrin, alpha 3 (antigen CD49C, alpha 3 subunit of VLA-3 receptor) | 17q21.33 |
| 3676 | ITGA4 | integrin, alpha 4 (antigen CD49D, alpha 4 subunit of VLA-4 receptor) | 2q31.3 |
| 3678 | ITGA5 | integrin, alpha 5 (fibronectin receptor, alpha polypeptide) | 12q11-q13 |
| 3679 | ITGA7 | integrin, alpha 7 | 12q13 |
| 3680 | ITGA9 | integrin, alpha 9 | 3p21.3 |
| 3685 | ITGAV | integrin, alpha V (vitronectin receptor, alpha polypeptide, antigen CD51) | 2q31-q32 |
| 3688 | ITGB1 | integrin, beta 1 (fibronectin receptor, beta polypeptide, antigen CD29 includes MDF2, MSK12) | 10p11.2 |
| 3690 | ITGB3 | integrin, beta 3 (platelet glycoprotein IIIa, antigen CD61) | 17q21.32 |
| 3691 | ITGB4 | integrin, beta 4 | 17q25 |
| 3693 | ITGB5 | integrin, beta 5 | 3q21.2 |
| 3694 | ITGB6 | integrin, beta 6 | 2q24.2 |
| 3695 | ITGB7 | integrin, beta 7 | 12q13.13 |
| 3696 | ITGB8 | integrin, beta 8 | 7p15.3 |
| 3725 | JUN | jun oncogene | 1p32-p31 |
| 3908 | LAMA2 | laminin, alpha 2 | 6q22-q23 |
| 3909 | LAMA3 | laminin, alpha 3 | 18q11.2 |
| 3910 | LAMA4 | laminin, alpha 4 | 6q21 |
| 3911 | LAMA5 | laminin, alpha 5 | 20q13.2-q13.3 |
| 3912 | LAMB1 | laminin, beta 1 | 7q22 |
| 3913 | LAMB2 | laminin, beta 2 (laminin S) | 3p21 |
| 3914 | LAMB3 | laminin, beta 3 | 1q32 |
| 3915 | LAMC1 | laminin, gamma 1 (formerly LAMB2) | 1q31 |
| 3918 | LAMC2 | laminin, gamma 2 | 1q25-q31 |
| 4023 | LPL | lipoprotein lipase | 8p22 |
| 4040 | LRP6 | low density lipoprotein receptor-related protein 6 | 12p11-p13 |
| 4041 | LRP5 | low density lipoprotein receptor-related protein 5 | 11q13.4 |
| 4052 | LTBP1 | latent transforming growth factor beta binding protein 1 | 2p22-p21 |
| 4053 | LTBP2 | latent transforming growth factor beta binding protein 2 | 14q24 |
| 4054 | LTBP3 | latent transforming growth factor beta binding protein 3 | 11q12 |
| 4060 | LUM | lumican | 12q21.3-q22 |
| 4086 | SMAD1 | SMAD family member 1 | 4q31 |
| 4087 | SMAD2 | SMAD family member 2 | 18q21.1 |
| 4088 | SMAD3 | SMAD family member 3 | 15q22.33 |
| 4089 | SMAD4 | SMAD family member 4 | 18q21.1 |
| 4089 | SMAD4 | SMAD family member 4 | 18q21.1 |
| 4090 | SMAD5 | SMAD family member 5 | 5q31 |
| 4091 | SMAD6 | SMAD family member 6 | 15q21-q22 |
| 4092 | SMAD7 | SMAD family member 7 | 18q21.1 |
| 4093 | SMAD9 | SMAD family member 9 | 13q12-q14 |
| 4146 | MATN1 | matrilin 1, cartilage matrix protein | 1p35 |
| 4147 | MATN2 | matrilin 2 | 8q22 |
| 4148 | MATN3 | matrilin 3 | 2p24-p23 |
| 4166 | CHST6 | carbohydrate (N-acetylglucosamine 6-O) sulfotransferase 6 | 16q22 |
| 4199 | ME1 | malic enzyme 1, NADP(+)-dependent, cytosolic | 6q12 |
| 4237 | MFAP2 | microfibrillar-associated protein 2 | 1p36.1-p35 |
| 4312 | MMP1 | matrix metallopeptidase 1 (interstitial collagenase) | 11q22.3 |
| 4313 | MMP2 | matrix metallopeptidase 2 (gelatinase A, 72 kDa gelatinase, 72 kDa type IV collagenase) | 16q13-q21 |
| 4314 | MMP3 | matrix metallopeptidase 3 (stromelysin 1, progelatinase) | 11q22.3 |

TABLE 1-continued

List of the markers taken into account for the chip experiments:

| Gene ID | Gene symbol | Description of the gene | Chromosome |
|---|---|---|---|
| 4316 | MMP7 | matrix metallopeptidase 7 (matrilysin, uterine) | 11q21-q22 |
| 4316 | MMP7 | matrix metallopeptidase 7 (matrilysin, uterine) | 11q21-q22 |
| 4319 | MMP10 | matrix metallopeptidase 10 (stromelysin 2) | 11q22.3 |
| 4320 | MMP11 | matrix metallopeptidase 11 (stromelysin 3) | 22q11.2 |
| 4321 | MMP12 | matrix metallopeptidase 12 (macrophage elastase) | 11q22.3 |
| 4322 | MMP13 | matrix metallopeptidase 13 (collagenase 3) | 11q22.3 |
| 4323 | MMP14 | matrix metallopeptidase 14 (membraneinserted) | 14q11-q12 |
| 4324 | MMP15 | matrix metallopeptidase 15 (membraneinserted) | 16q13-q21 |
| 4609 | MYC | v-myc myelocytomatosis viral oncogene homolog (avian) | 8q24.21 |
| 4772 | NFATC1 | nuclear factor of activated T-cells, cytoplasmic, calcineurin-dependent 1 | 18q23 |
| 4773 | NFATC2 | nuclear factor of activated T-cells, cytoplasmic, calcineurin-dependent 2 | 20q13.2-q13.3 |
| 4775 | NFATC3 | nuclear factor of activated T-cells, cytoplasmic, calcineurin-dependent 3 | 16q22.2 |
| 4776 | NFATC4 | nuclear factor of activated T-cells, cytoplasmic, calcineurin-dependent 4 | 14q11.2 |
| 4838 | NODAL | nodal homolog (mouse) | 10q22.1 |
| 4973 | OLR1 | oxidized low density lipoprotein (lectin-like) receptor 1 | 12p13.2-p12.3 |
| 4982 | TNFRSF11B | tumor necrosis factor receptor superfamily, member 11b | 8q24 |
| 5054 | SERPINE1 | serpin peptidase inhibitor, clade E (nexin, plasminogen activator inhibitor type 1), member 1 | 7q21.3-q22 |
| 5055 | SERPINB2 | serpin peptidase inhibitor, clade B (ovalbumin), member 2 | 18q21.3 |
| 5105 | PCK1 | phosphoenolpyruvate carboxykinase 1 (soluble) | 20q13.31 |
| 5106 | PCK2 | phosphoenolpyruvate carboxykinase 2 (mitochondrial) | 14q12 |
| 5170 | PDPK1 | 3-phosphoinositide dependent protein kinase-1 | 16p13.3 |
| 5308 | PITX2 | paired-like homeodomain 2 | 4q25-q27 |
| 5327 | PLAT | plasminogen activator, tissue | 8p12 |
| 5330 | PLCB2 | phospholipase C, beta 2 | 15q15 |
| 5331 | PLCB3 | phospholipase C, beta 3 (phosphatidylinositolspecific) | 11q13 |
| 5332 | PLCB4 | phospholipase C, beta 4 | 20p12 |
| 5346 | PLIN | perilipin | 15q26 |
| 5360 | PLTP | phospholipid transfer protein | 20q12-q13.1 |
| 5465 | PPARA | peroxisome proliferator-activated receptor alpha | 22q12-q13.1 |
| 5467 | PPARD | peroxisome proliferator-activated receptor delta | 6p21.2-p21.1 |
| 5468 | PPARG | peroxisome proliferator-activated receptor gamma | 3p25 |
| 5515 | PPP2CA | protein phosphatase 2 (formerly 2A), catalytic subunit, alpha isoform | 5q31.1 |
| 5516 | PPP2CB | protein phosphatase 2 (formerly 2A), catalytic subunit, beta isoform | 8p12 |
| 5518 | PPP2R1A | protein phosphatase 2 (formerly 2A), regulatory subunit A, alpha isoform | 19q13.33 |
| 5519 | PPP2R1B | protein phosphatase 2 (formerly 2A), regulatory subunit A, beta isoform | 11q23.2 |
| 5525 | PPP2R5A | protein phosphatase 2, regulatory subunit B', alpha isoform | 1q32.2-q32.3 |
| 5526 | PPP2R5B | protein phosphatase 2, regulatory subunit B', beta isoform | 11q12-q13 |
| 5527 | PPP2R5C | protein phosphatase 2, regulatory subunit B', gamma isoform | 14q32 |
| 5528 | PPP2R5D | protein phosphatase 2, regulatory subunit B', delta isoform | 6p21.1 |
| 5529 | PPP2R5E | protein phosphatase 2, regulatory subunit B', epsilon isoform | 14q23.1 |
| 5530 | PPP3CA | protein phosphatase 3 (formerly 2B), catalytic subunit, alpha isoform | 4q21-q24 |
| 5532 | PPP3CB | protein phosphatase 3 (formerly 2B), catalytic subunit, beta isoform | 10q21-q22 |
| 5533 | PPP3CC | protein phosphatase 3 (formerly 2B), catalytic subunit, gamma isoform | 8p21.3 |
| 5534 | PPP3R1 | protein phosphatase 3 (formerly 2B), regulatory subunit B, alpha isoform | 2p15 |
| 5535 | PPP3R2 | protein phosphatase 3 (formerly 2B), regulatory subunit B, beta isoform | 9q31.1 |
| 5566 | PRKACA | protein kinase, cAMP-dependent, catalytic, alpha | 19p13.1 |
| 5567 | PRKACB | protein kinase, cAMP-dependent, catalytic, beta | 1p36.1 |
| 5568 | PRKACG | protein kinase, cAMP-dependent, catalytic, gamma | 9q13 |
| 5578 | PRKCA | protein kinase C, alpha | 17q22-q23.2 |
| 5579 | PRKCB | protein kinase C, beta | 16p11.2 |

TABLE 1-continued

List of the markers taken into account for the chip experiments:

| Gene ID | Gene symbol | Description of the gene | Chromosome |
|---|---|---|---|
| 5582 | PRKCG | protein kinase C, gamma | 19q13.4 |
| 5594 | MAPK1 | mitogen-activated protein kinase 1 | 22q11.2 |
| 5595 | MAPK3 | mitogen-activated protein kinase 3 | 16p11.2 |
| 5599 | MAPK8 | mitogen-activated protein kinase 8 | 10q11.22 |
| 5601 | MAPK9 | mitogen-activated protein kinase 9 | 5q35 |
| 5602 | MAPK10 | mitogen-activated protein kinase 10 | 4q22.1-q23 |
| 5613 | PRKX | protein kinase, X-linked | Xp22.3 |
| 5616 | PRKY | protein kinase, Y-linked | Yp11.2 |
| 5649 | RELN | reelin | 7q22 |
| 5663 | PSEN1 | presenilin 1 | 14q24.3 |
| 5879 | RAC1 | ras-related C3 botulinum toxin substrate 1 (rho family, small GTP binding protein Rac1) | 7p22 |
| 5880 | RAC2 | ras-related C3 botulinum toxin substrate 2 (rho family, small GTP binding protein Rac2) | 22q13.1 |
| 5881 | RAC3 | ras-related C3 botulinum toxin substrate 3 (rho family, small GTP binding protein Rac3) | 17q25.3 |
| 5933 | RBL1 | retinoblastoma-like 1 (p107) | 20q11.2 |
| 5934 | RBL2 | retinoblastoma-like 2 (p130) | 16q12.2 |
| 5950 | RBP4 | retinol binding protein 4, plasma | 10q23-q24 |
| 6093 | ROCK1 | Rho-associated, coiled-coil containing protein kinase 1 | 18q11.1 |
| 6198 | RPS6KB1 | ribosomal protein S6 kinase, 70 kDa, polypeptide 1 | 17q23.1 |
| 6199 | RPS6KB2 | ribosomal protein S6 kinase, 70 kDa, polypeptide 2 | 11q13.1 |
| 6256 | RXRA | retinoid X receptor, alpha | 9q34.3 |
| 6257 | RXRB | retinoid X receptor, beta | 6p21.3 |
| 6258 | RXRG | retinoid X receptor, gamma | 1q22-q23 |
| 6319 | SCD | stearoyl-CoA desaturase (delta-9-desaturase) | 10q24.31 |
| 6342 | SCP2 | sterol carrier protein 2 | 1p32 |
| 6382 | SDC1 | syndecan 1 | 2p24.1 |
| 6383 | SDC2 | syndecan 2 | 8q22-q23 |
| 6385 | SDC4 | syndecan 4 | 20q12 |
| 6422 | SFRP1 | secreted frizzled-related protein 1 | 8p12-p11.1 |
| 6423 | SFRP2 | secreted frizzled-related protein 2 | 4q31.3 |
| 6424 | SFRP4 | secreted frizzled-related protein 4 | 7p14.1 |
| 6425 | SFRP5 | secreted frizzled-related protein 5 | 10q24.1 |
| 6477 | SIAH1 | seven in absentia homolog 1 (Drosophila) | 16q12 |
| 6482 | ST3GAL1 | ST3 beta-galactoside alpha-2,3sialyltransferase 1 | 8q24.22 |
| 6483 | ST3GAL2 | ST3 beta-galactoside alpha-2,3sialyltransferase 2 | 16q22.1 |
| 6487 | ST3GAL3 | ST3 beta-galactoside alpha-2,3sialyltransferase 3 | 1p34.1 |
| 6500 | SKP1 | S-phase kinase-associated protein 1 | 5q31 |
| 6667 | SP1 | Sp1 transcription factor | 12q13.1 |
| 6696 | SPP1 | secreted phosphoprotein 1 | 4q21-q25 |
| 6885 | MAP3K7 | mitogen-activated protein kinase kinase kinase 7 | 6q16.1-q16.3 |
| 6907 | TBL1X | transducin (beta)-like 1X-linked | Xp22.3 |
| 6932 | TCF7 | transcription factor 7 (T-cell specific, HMG-box) | 5q31.1 |
| 6934 | TCF7L2 | transcription factor 7-like 2 (T-cell specific, HMG-box) | 10q25.3 |
| 7027 | TFDP1 | transcription factor Dp-1 | 13q34 |
| 7040 | TGFB1 | transforming growth factor, beta 1 | 19q13.2 |
| 7042 | TGFB2 | transforming growth factor, beta 2 | 1q41 |
| 7043 | TGFB3 | transforming growth factor, beta 3 | 14q24 |
| 7044 | LEFTY2 | left-right determination factor 2 | 1q42.1 |
| 7046 | TGFBR1 | transforming growth factor, beta receptor 1 | 9q22 |
| 7048 | TGFBR2 | transforming growth factor, beta receptor II (70/80 kDa) | 3p22 |
| 7057 | THBS1 | thrombospondin 1 | 15q15 |
| 7058 | THBS2 | thrombospondin 2 | 6q27 |
| 7059 | THBS3 | thrombospondin 3 | 1q21 |
| 7060 | THBS4 | thrombospondin 4 | 5q13 |
| 7076 | TIMP1 | TIMP metallopeptidase inhibitor 1 | Xp11.3-p11.23 |
| 7077 | TIMP2 | TIMP metallopeptidase inhibitor 2 | 17q25 |
| 7124 | TNF | tumor necrosis factor (TNF superfamily, member 2) | 6p21.3 |
| 7143 | TNR | tenascin R (restrictin, janusin) | 1q24 |
| 7146 | TNXA | tenascin XA pseudogene | 6p21.3 |
| 7148 | TNXB | tenascin XB | 6p21.3 |
| 7157 | TP53 | tumor protein p53 | 17p13.1 |
| 7316 | UBC | ubiquitin C | 12q24.3 |
| 7350 | UCP1 | uncoupling protein 1 (mitochondrial, proton carrier) | 4q28-q31 |
| 7448 | VTN | vitronectin | 17q11 |
| 7450 | VWF | von Willebrand factor | 12p13.3 |
| 7471 | WNT1 | wingless-type MMTV integration site family, member 1 | 12q13 |
| 7472 | WNT2 | wingless-type MMTV integration site family member 2 | 7q31.2 |

TABLE 1-continued

List of the markers taken into account for the chip experiments:

| Gene ID | Gene symbol | Description of the gene | Chromosome |
|---|---|---|---|
| 7473 | WNT3 | wingless-type MMTV integration site family, member 3 | 17q21 |
| 7474 | WNT5A | wingless-type MMTV integration site family, member 5A | 3p21-p14 |
| 7475 | WNT6 | wingless-type MMTV integration site family, member 6 | 2q35 |
| 7476 | WNT7A | wingless-type MMTV integration site family, member 7A | 3p25 |
| 7477 | WNT7B | wingless-type MMTV integration site family, member 7B | 22q13 |
| 7478 | WNT8A | wingless-type MMTV integration site family, member 8A | 5q31 |
| 7479 | WNT8B | wingless-type MMTV integration site family, member 8B | 10q24 |
| 7480 | WNT10B | wingless-type MMTV integration site family, member 10B | 12q13 |
| 7481 | WNT11 | wingless-type MMTV integration site family, member 11 | 11q13.5 |
| 7482 | WNT2B | wingless-type MMTV integration site family, member 2B | 1p13 |
| 7483 | WNT9A | wingless-type MMTV integration site family, member 9A | 1q42 |
| 7484 | WNT9B | wingless-type MMTV integration site family, member 9B | 17q21 |
| 7498 | XDH | xanthine dehydrogenase | 2p23.1 |
| 7839 | LSL | Leptin, serum levels of | 2p21 |
| 7855 | FZD5 | frizzled homolog 5 (*Drosophila*) | 2q33-q34 |
| 7976 | FZD3 | frizzled homolog 3 (*Drosophila*) | 8p21 |
| 8061 | FOSL1 | FOS-like antigen 1 | 11q13 |
| 8200 | GDF5 | growth differentiation factor 5 | 20q11.2 |
| 8215 | DVL1L1 | dishevelled, dsh homolog 1 (*Drosophila*)-like 1 | 22q11.21 |
| 8309 | ACOX2 | acyl-Coenzyme A oxidase 2, branched chain | 3p14.3 |
| 8310 | ACOX3 | acyl-Coenzyme A oxidase 3, pristanoyl | 4p15.3 |
| 8312 | AXIN1 | axin 1 | 16p13.3 |
| 8313 | AXIN2 | axin 2 | 17q23-q24 |
| 8321 | FZD1 | frizzled homolog 1 (*Drosophila*) | 7q21 |
| 8322 | FZD4 | frizzled homolog 4 (*Drosophila*) | 11q14.2 |
| 8323 | FZD6 | frizzled homolog 6 (*Drosophila*) | 8q22.3-q23.1 |
| 8324 | FZD7 | frizzled homolog 7 (*Drosophila*) | 2q33 |
| 8325 | FZD8 | frizzled homolog 8 (*Drosophila*) | 10p11.21 |
| 8326 | FZD9 | frizzled homolog 9 (*Drosophila*) | 7q11.23 |
| 8425 | LTBP4 | latent transforming growth factor beta binding protein 4 | 19q13.1-q13.2 |
| 8454 | CUL1 | cullin 1 | 7q36.1 |
| 8509 | NDST2 | N-deacetylase/N-sulfotransferase (heparan glucosaminyl) 2 | 10q22 |
| 8515 | ITGA10 | integrin, alpha 10 | 1q21 |
| 8516 | ITGA8 | integrin, alpha 8 | 10p13 |
| 8534 | CHST1 | carbohydrate (keratan sulfate Gal-6) sulfotransferase 1 | 11p11.2-p11.1 |
| 8607 | RUVBL1 | RuvB-like 1 (*E. coli*) | 3q21 |
| 8646 | CHRD | chordin | 3q27 |
| 8649 | MAPKSP1 | MAPK scaffold protein 1 | 4q23 |
| 8702 | B4GALT4 | UDP-Gal:betaGlcNAc beta 1,4-galactosyltransferase, polypeptide 4 | 3q13.3 |
| 8703 | B4GALT3 | UDP-Gal:betaGlcNAc beta 1,4-galactosyltransferase, polypeptide 3 | 1q21-q23 |
| 8704 | B4GALT2 | UDP-Gal:betaGlcNAc beta 1,4-galactosyltransferase, polypeptide 2 | 1p34-p33 |
| 8759 | ADAM1 | ADAM metallopeptidase domain 1 (pseudogene) | 12q24.13 |
| 8785 | MATN4 | matrilin 4 | 20q13.1-q13.2 |
| 8945 | BTRC | beta-transducin repeat containing | 10q24.32 |
| 9241 | NOG | noggin | 17q21-q22 |
| 9348 | NDST3 | N-deacetylase/N-sulfotransferase (heparan glucosaminyl) 3 | 4q26 |
| 9350 | CER1 | cerberus 1, cysteine knot superfamily, homolog (*Xenopus laevis*) | 9p23-p22 |
| 9370 | ADIPOQ | adiponectin, C1Q and collagen domain containing | 3q27 |
| 9372 | ZFYVE9 | zinc finger, FYVE domain containing 9 | 1p32.3 |
| 9394 | HS6ST1 | heparan sulfate 6-O-sulfotransferase 1 | 2q21 |
| 9415 | FADS2 | fatty acid desaturase 2 | 11q12-q13.1 |
| 9435 | CHST2 | carbohydrate (N-acetylglucosamine-6-O) sulfotransferase 2 | 3q24 |
| 9469 | CHST3 | carbohydrate (chondroitin 6) sulfotransferase 3 | 10q22.1 |
| 9475 | ROCK2 | Rho-associated, coiled-coil containing protein kinase 2 | 2p24 |

TABLE 1-continued

List of the markers taken into account for the chip experiments:

| Gene ID | Gene symbol | Description of the gene | Chromosome |
|---|---|---|---|
| 9653 | HS2ST1 | heparan sulfate 2-O-sulfotransferase 1 | 1p31.1-p22.1 |
| 9672 | SDC3 | syndecan 3 | 1pter-p22.3 |
| 9765 | ZFYVE16 | zinc finger, FYVE domain containing 16 | 5q14 |
| 9899 | SV2B | synaptic vesicle glycoprotein 2B | 15q26.1 |
| 9900 | SV2A | synaptic vesicle glycoprotein 2A | 1q21.2 |
| 9953 | HS3ST3B1 | heparan sulfate (glucosamine) 3-Osulfotransferase 3B1 | 17p12-p11.2 |
| 9955 | HS3ST3A1 | heparan sulfate (glucosamine) 3-Osulfotransferase 3A1 | 17p12-p11.2 |
| 9956 | HS3ST2 | heparan sulfate (glucosamine) 3-Osulfotransferase 2 | 16p12 |
| 9957 | HS3ST1 | heparan sulfate (glucosamine) 3-Osulfotransferase 1 | 4p16 |
| 9978 | RBX1 | ring-box 1 | 22q13.2 |
| 10023 | FRAT1 | frequently rearranged in advanced T-cell lymphomas | 10q24.1 |
| 10062 | NR1H3 | nuclear receptor subfamily 1, group H, member 3 | 11p11.2 |
| 10090 | UST | uronyl-2-sulfotransferase | 6q25.1 |
| 10135 | NAMPT | nicotinamide phosphoribosyltransferase | 7q22.2 |
| 10164 | CHST4 | carbohydrate (N-acetylglucosamine 6-O) sulfotransferase 4 | 16q22.3 |
| 10297 | APC2 | adenomatosis polyposis coli 2 | 19p13.3 |
| 10319 | LAMC3 | laminin, gamma 3 | 9q31-q34 |
| 10468 | FST | follistatin | 5q11.2 |
| 10580 | SORBS1 | sorbin and SH3 domain containing 1 | 10q23.3-q24.1 |
| 10637 | LEFTY1 | left-right determination factor 1 | 1q42.1 |
| 10678 | B3GNT2 | UDP-GlcNAc:betaGal beta-1,3-Nacetylglucosaminyltransferase 2 | 2p15 |
| 10725 | NFAT5 | nuclear factor of activated T-cells 5, tonicityresponsive | 16q22.1 |
| 10998 | SLC27A5 | solute carrier family 27 (fatty acid transporter), member 5 | 19q13.43 |
| 10999 | SLC27A4 | solute carrier family 27 (fatty acid transporter), member 4 | 9q34.11 |
| 11001 | SLC27A2 | solute carrier family 27 (fatty acid transporter), member 2 | 15q21.2 |
| 11041 | B3GNT1 | UDP-GlcNAc:betaGal beta-1,3-Nacetylglucosaminyltransferase 1 | 11q13.1 |
| 11197 | WIF1 | WNT inhibitory factor 1 | 12q14.3 |
| 11211 | FZD10 | frizzled homolog 10 (*Drosophila*) | 12q24.33 |
| 11285 | B4GALT7 | xylosylprotein beta 1,4-galactosyltransferase, polypeptide 7 (galactosyltransferase I) | 5q35.2-q35.3 |
| 22798 | LAMB4 | laminin, beta 4 | 7q22-q31.2 |
| 22801 | ITGA11 | integrin, alpha 11 | 15q23 |
| 22856 | CHSY1 | chondroitin sulfate synthase 1 | 15q26.3 |
| 22927 | HABP4 | hyaluronan binding protein 4 | 9q22.3-q31 |
| 22943 | DKK1 | dickkopf homolog 1 (*Xenopus laevis*) | 10q11.2 |
| 22987 | SV2C | synaptic vesicle glycoprotein 2C | 5q13.3 |
| 23002 | DAAM1 | dishevelled associated activator of morphogenesis 1 | 14q23.1 |
| 23236 | PLCB1 | phospholipase C, beta 1 (phosphoinositidespecific) | 20p12 |
| 23291 | FBXW11 | F-box and WD repeat domain containing 11 | 5q35.1 |
| 23305 | ACSL6 | acyl-CoA synthetase long-chain family member 6 | 5q31 |
| 23401 | FRAT2 | frequently rearranged in advanced T-cell lymphomas 2 | 10q24.1 |
| 23500 | DAAM2 | dishevelled associated activator of morphogenesis 2 | 6p21.2 |
| 26035 | GLCE | glucuronic acid epimerase | 15q23 |
| 26229 | B3GAT3 | beta-1,3-glucuronyltransferase 3 (glucuronosyltransferase I) | 11q12.3 |
| 27087 | B3GAT1 | beta-1,3-glucuronyltransferase 1 (glucuronosyltransferase P) | 11q25 |
| 27101 | CACYBP | calcyclin binding protein | 1q24-q25 |
| 27121 | DKK4 | dickkopf homolog 4 (*Xenopus laevis*) | 8p11.2-p11.1 |
| 27123 | DKK2 | dickkopf homolog 2 (*Xenopus laevis*) | 4q25 |
| 28965 | SLC27A6 | solute carrier family 27 (fatty acid transporter), member 6 | 5q23.3 |
| 29940 | DSE | dermatan sulfate epimerase | 6q22 |
| 50509 | COL5A3 | collagen, type V, alpha 3 | 19p13.2 |
| 50515 | CHST11 | carbohydrate (chondroitin 4) sulfotransferase 11 | 12q |
| 51129 | ANGPTL4 | angiopoietin-like 4 | 19p13.3 |
| 51176 | LEF1 | lymphoid enhancer-binding factor 1 | 4q23-q25 |
| 51206 | GP6 | glycoprotein VI (platelet) | 19q13.4 |
| 51384 | WNT16 | wingless-type MMTV integration site family, member 16 | 7q31 |
| 51701 | NLK | nemo-like kinase | 17q11.2 |
| 51703 | ACSL5 | acyl-CoA synthetase long-chain family member 5 | 10q25.1-q25.2 |

TABLE 1-continued

List of the markers taken into account for the chip experiments:

| Gene ID | Gene symbol | Description of the gene | Chromosome |
| --- | --- | --- | --- |
| 54361 | WNT4 | wingless-type MMTV integration site family, member 4 | 1p36.23-p35.1 |
| 55454 | CSGALNACT2 | chondroitin sulfate N-acetylgalactosaminyltransferase 2 | 10q11.21 |
| 55501 | CHST12 | carbohydrate (chondroitin 4) sulfotransferase 12 | 7p22 |
| 55790 | CSGALNACT1 | chondroitin sulfate N-acetylgalactosaminyltransferase 1 | 8p21.3 |
| 56548 | CHST7 | carbohydrate (N-acetylglucosamine 6-O) sulfotransferase 7 | Xp11.23 |
| 56729 | RETN | resistin | 19p13.2 |
| 56998 | CTNNBIP1 | catenin, beta interacting protein 1 | 1p36.22 |
| 57154 | SMURF1 | SMAD specific E3 ubiquitin protein ligase 1 | 7q22.1 |
| 57216 | VANGL2 | vang-like 2 (van gogh, *Drosophila*) | 1q22-q23 |
| 57680 | CHD8 | chromodomain helicase DNA binding protein 8 | 14q11.2 |
| 58496 | LY6G5B | lymphocyte antigen 6 complex, locus G5B | 6p21.3 |
| 59343 | SENP2 | SUMO1/sentrin/SMT3 specific peptidase 2 | 3q27.2 |
| 63923 | TNN | tenascin N | 1q23-q24 |
| 64131 | XYLT1 | xylosyltransferase I | 16p12.3 |
| 64132 | XYLT2 | xylosyltransferase II | 17q21.3-q22 |
| 64321 | SOX17 | SRY (sex determining region Y)-box 17 | 8q11.23 |
| 64579 | NDST4 | N-deacetylase/N-sulfotransferase (heparan glucosaminyl) 4 | 4q25-q26 |
| 64750 | SMURF2 | SMAD specific E3 ubiquitin protein ligase 2 | 17q22-q23 |
| 64840 | PORCN | porcupine homolog (*Drosophila*) | Xp11.23 |
| 79586 | CHPF | chondroitin polymerizing factor | 2q35 |
| 79718 | TBL1XR1 | transducin (beta)-like 1 X-linked receptor 1 | 3q26.32 |
| 79966 | SCD5 | stearoyl-CoA desaturase 5 | 4q21.22 |
| 80070 | ADAMTS20 | ADAM metallopeptidase with thrombospondin type 1 motif, 20 | 12q12 |
| 80319 | CXXC4 | CXXC finger 4 | 4q22-q24 |
| 80326 | WNT10A | wingless-type MMTV integration site family, member 10A | 2q35 |
| 81029 | WNT5B | wingless-type MMTV integration site family, member 5B | 12p13.3 |
| 81839 | VANGL1 | vang-like 1 (van gogh, *Drosophila*) | 1p11-p13.1 |
| 83439 | TCF7L1 | transcription factor 7-like 1 (T-cell specific, HMG-box) | 2p11.2 |
| 83729 | INHBE | inhibin, beta E | 12q13.3 |
| 85407 | NKD1 | naked cuticle homolog 1 (*Drosophila*) | 16q12 |
| 85409 | NKD2 | naked cuticle homolog 2 (*Drosophila*) | 5p15.3 |
| 89780 | WNT3A | wingless-type MMTV integration site family, member 3A | 1q42 |
| 90161 | HS6ST2 | heparan sulfate 6-O-sulfotransferase 2 | Xq26.2 |
| 90665 | TBL1Y | transducin (beta)-like 1Y-linked | Yp11.2 |
| 93010 | B3GNT7 | UDP-GlcNAc:betaGal beta-1,3-N-acetylglucosaminyltransferase 7 | 2q37.1 |
| 113189 | CHST14 | carbohydrate (N-acetylgalactosamine 4-0) sulfotransferase 14 | 15q15.1 |
| 116519 | APOA5 | apolipoprotein A-V | 11q23 |
| 122011 | CSNK1A1L | casein kinase 1, alpha 1-like | 13q13.3 |
| 126129 | CPT1C | carnitine palmitoyltransferase 1C | 19q13.33 |
| 126792 | B3GALT6 | UDP-Gal:betaGal beta 1,3-galactosyltransferase polypeptide 6 | 1p36.33 |
| 130399 | ACVR1C | activin A receptor, type IC | 2q24.1 |
| 135152 | B3GAT2 | beta-1,3-glucuronyltransferase 2 (glucuronosyltransferase S) | 6q13 |
| 144165 | PRICKLE1 | prickle homolog 1 (*Drosophila*) | 12q12 |
| 151449 | GDF7 | growth differentiation factor 7 | 2p24.1 |
| 166012 | CHST13 | carbohydrate (chondroitin 4) sulfotransferase 13 | 3q21.3 |
| 166336 | PRICKLE2 | prickle homolog 2 (*Drosophila*) | 3p14.1 |
| 222537 | HS3ST5 | heparan sulfate (glucosamine) 3-O-sulfotransferase 5 | 6q22.31 |
| 266722 | HS6ST3 | heparan sulfate 6-O-sulfotransferase 3 | 13q32.1 |
| 283106 | CSNK2A1P | casein kinase 2, alpha 1 polypeptide pseudogene | 11p15.3 |
| 284217 | LAMA1 | laminin, alpha 1 | 18p11.31 |
| 284541 | CYP4A22 | cytochrome P450, family 4, subfamily A, polypeptide 22 | 1p33 |
| 337876 | CHSY3 | chondroitin sulfate synthase 3 | 5q23.3 |
| 353500 | BMP8A | bone morphogenetic protein 8a | 1p34.2 |
| 375790 | AGRN | agrin | 1p36.33 |
| 376497 | SLC27A1 | solute carrier family 27 (fatty acid transporter), member 1 | 19p13.11 |
| 392255 | GDF6 | growth differentiation factor 6 | 8q22.1 |
| 642956 | FABP5L9 | fatty acid binding protein 5-like 9 | 15q25.3 |
| 728641 | FABP5L7 | fatty acid binding protein 5-like 7 | 11q12.1 |

TABLE 1-continued

List of the markers taken into account for the chip experiments:

| Gene ID | Gene symbol | Description of the gene | Chromosome |
|---------|-------------|-------------------------|------------|
| 728729 | FABP5L8 | fatty acid binding protein 5-like 8 | 15q25.2 |
| 729163 | FABP5L2 | fatty acid binding protein 5-like 2 | 13q14.3 |

Human Primary Cells

Human dermal fibroblasts or human subcutaneous preadipocytes in the form of in vitro cell culture systems are used as biological test systems. Both cell types are commercially available (the company Lifeline or the company CellApplications).

Human dermal fibroblasts are as a rule obtained from the dermis of neonatal donors (phimoses) or from the skin of adult donors. They are always noninfectious donor materials, which were isolated by the respective supplier from the in vivo tissue dressing and were expanded singly in a corresponding cell culture medium. Cryopreserved human dermal fibroblasts can, after seeding in suitable cell culture media, go through up to 16 doubling cycles without impairment of their typical physiology and morphology. Human dermal fibroblasts occur in all connective tissue structures and are a well-characterized in vitro test system. They release extracellular matrix proteins in vitro and are suitable in in vitro research in particular also for investigating fibroblast growth, investigation of the differentiation of fibroblasts and also in particular for investigating collagen metabolism in the context of wound healing. It has been shown in various ways that human dermal fibroblasts are suitable for the population of in vitro reconstituted, three-dimensional dermis equivalents and in vitro reconstituted human skin models.

Human preadipocytes (HPAd) are usually obtained from human fat tissue of noninfectious donors. Whereas human adipocytes are not suitable for cryopreservation and therefore also not for possible reseeding after extraction of the cells from the donor tissue, after corresponding extraction, human preadipocytes can be cryopreserved very well and can undergo in vitro cultivation. However, they cannot be passaged more often than twice. After that, they differentiate into human adipocytes. Human preadipocytes are characterized by a morphology that closely resembles the morphology of human dermal fibroblasts. Human adipocytes that were obtained by in vitro differentiation from human preadipocytes can be used as an in vitro test system for investigating insulin-stimulated glucose transport, for characterizing hormone-controlled lipolysis and for investigating gene expression in fat tissues. The HPAd/HAd system is an extremely well characterized in vitro test system for investigating the causes of adiposity and type II diabetes.

Contacting the Human Cells with Yeast Extract

Human prim. fibroblasts were expanded in medium 199 (Souto L R, Rehder J, Vassallo J, Cintra M L, Kraemer M H, Puzzi M B (2006) Sao Paulo Med J. 124(2), 71-6. Model for human skin reconstructed in vitro composed of associated dermis and epidermis; E. Pinney, K. Liu, B. Sheeman and J. Mansbridge (2001): Human three-dimensional fibroblast cultures express angiogenic activity. J Cell Physiol 183, 74-82) up to 75% subconfluence with 10% FCS (fetal calf serum) and 2% penicillin (Pen)/streptomycin (Strep). After cell harvesting, the cells were integrated into the extracellular collagen matrix (ECM) and were cultured in the presence of M199 medium with 5% FCS and 2% Pen/Strep. Exposure with the active substance (yeast extract) took place 4-5 days after seeding the cells in the ECM for a period of 24-48 h. Cell viability was monitored during cultivation using the standard MTT test (Mosmann, Tim "Rapid colorimetric assay for cellular growth and survival: application to proliferation and cytotoxicity assays". Journal of Immunological Methods 65 (1-2): 55-63). Normal cell culture conditions (5% $CO_2$; 37° C., max. humidity) were selected.

Human preadipocytes were expanded in normal cell culture conditions and using a special growth medium (supplier: Cell Applications) up to 60-75% subconfluence. Differentiation of the cells to adipocytes was inhibited. After harvesting the cells and reseeding in 6-well plates (>10 000 cells/cm$^2$), the cells were cultured for 24-48 h in the presence of the growth medium and were then differentiated using a special differentiation medium (supplier: Cell Applications). Differentiation took place for a period of 10-14 days in the presence of the yeast extract ("repeated dose" continuously every 5-7 days).

The cells in co-culture were in each case expanded as described above. 48 h after integration of the fibroblasts into the ECM (as described above), the hum. preadipocytes were applied on the collagen matrix. The whole construct was cultured in normal cell culture conditions and using the (pre)adipocyte growth medium for a further 48 h. Then differentiation of the preadipocytes took place in the presence of the active substance using the differentiation medium. The cell viability of both cell types was once again monitored with the standard MTT test. Release of intracellular lactate dehydrogenase (LDH) was determined quantitatively to assess the integrity of the cell membranes.

Human epidermal keratinocytes were expanded in Medium 154 from Cascade Biologics (Invitrogen Company). After reaching 70-80% subconfluence, the cells were harvested and were submerged-cultured in the presence of the medium described above on a polycarbonate membrane (<0.4 µM pore size) for a period of >48 h. The medium was additionally supplemented with FCS, and a BSA (bovine serum albumin) : fatty acid complex and vitamin E; L-serine and L-carnitine. Then there was shift of the cells to the air/medium boundary layer and transfer to a serum-free differentiation medium with increased $Ca^{2+}$ ion concentration with addition of vitamin C. The cells were cultured starting from the 7th day up to the 14th day of this airlift culture in the presence of the active substance ("repeated dose" continuously, daily). Normal cell culture conditions were also selected in this case.

Isolation of the RNA from the Fibroblasts

The total RNA is isolated from the fibroblasts using the RNeasy Mini Kit. For the analysis, the frozen fibroblasts are homogenized with a 5 mm steel ball, 300 µL RLT buffer and with 10 µl/mL beta mercaptoethanol in the Tissuelyser for 3 min at 16 000 Hz. The samples are centrifuged briefly, to bring down the foam in the Eppendorf cap. After addition of 590 µL RNase-free water and 10 µL protease K, the solution is digested for 10 min at 55° C. in the thermo-shaker. The supernatant of approx. 900 µL is put in a new Eppendorf cap and 450 µL of 96% ethanol is added. 700 µL is withdrawn, transferred to an RNeasy Mini Spin Column and centrifuged at 10 000 rev/min for 15 s at room temperature; the liquid can be discarded. Repeat this step with the liquid that remains. Then 700 μL of buffer RW1 is put in the RNeasy Mini Spin Column and centrifuged at 10 000 rev/min for 15 s at room temperature; the liquid can be discarded. The RNeasy Mini Spin Columns are put on a new tube (2.2 mL), 500 μL buffer RPE is added and centrifuged again for 15 s at 10 000 rev/min; the liquid is discarded. Now 500 μL of buffer RPE is added, and it is centrifuged at 10 000 rev/min at room temperature for 2 min; the liquid is discarded. The RNeasy Mini Spin Columns are put on a new tube (2.2 mL) and centrifuged at room temperature for 1 min at 13 000 rev/min until dry. The RNeasy Mini Spin Columns are put on an Eppendorf cap (1.5 mL) and 30 μL of RNase-free water is put directly on the membrane. Then it is centrifuged at 10 000 rev/min for 1 min. For measurement, 3 μL of RNA solution is investigated on the bioanalyser. The remaining solution is divided up (5 μL portions) and stored in the freezer at −80° C.

Isolation of the RNA from the Adipocytes

The total RNA is isolated from the adipocytes using the RNeasy Mini Kit. For this, the differentiation/exposure medium is removed quantitatively from the adipocytes by decanting. For lysis of the cells and release of the cytosolic RNA, the adipocytes are incubated in the 6-well cell culture plates for a period of 2 min at RT in the presence of a buffer containing guanidinium hydrochloride (V=600 μL; Qiagen buffer RLT). For complete disruption of the cells, the cell suspension is sheared by means of a 1 mL disposable syringe and a disposable injection cannula (0.60×30 mm; 23 G×1¼). The cell-free extract is transferred quantitatively to a 2-mL reaction vessel. The total RNA is precipitated by adding one volume of ethanol (70%). Then 700 μL of the precipitated lysate is transferred to an RNeasy Mini Column and centrifuged at >8000×g for 15 s. The total RNA binds to the column material. The flow-through is discarded. The same procedure is followed with the remaining volume of the lysate. Then 700 μL of a washing buffer (Qiagen buffer RW1) is added and it is centrifuged at ≥8000×g for 15 s. Once again, the flow-through is discarded. Then the columns are washed twice with 500 μL of an ethanol-containing buffer (Qiagen buffer RPE). The first washing operation takes place by centrifugation for a period of 15 s at ≥8000×g (the flow-through is discarded) and the second washing operation takes place for a period of 2 min at >8000×g (the flow-through is again discarded). For complete drying of the column material, the extraction columns are transferred to new collecting vessels and centrifuged for a period of 1 min at 8000×g. The extraction columns are then transferred to 1.5-mL reaction vessels and the total RNA bound to the columns is rehydrated by adding 50 μL water (RNase-free). Final elution of the total RNA then takes place by another centrifugation step (1 min at >8000 x g). For measurement, 90 μL water is added to 10 μL RNA solution and the absorption is measured at a wavelength of 260 nm. An absorption (A260) of 1.00 corresponds to a concentration of 50 μg/mL of double-stranded DNA, 33 μg/mL of short, single-stranded DNA or 40 μg/mL RNA. The remaining 40 μL of solution is divided up (10 μL portions) and stored in the freezer at −80° C.

Chip Technology

The isolated mRNA is investigated by biochip. For this biochip, 500 biomarkers (see Table 1) were selected and their specific pathway was investigated. The biochip was developed by the company Febit Biomed GmbH in Heidelberg. Five different samples were produced for each biomarker and six technical replicas for each sample, so that there are 30 replicas for each biomarker. The Geniom biochip was synthesized with the Geniom One Instrument using the standard kit for oligonucleotide syntheses. The light-activated in-situ oligonucleotide synthesis is connected with a digital Micromirror unit to the Geniom One Instrument on an activated three-dimensional reaction carrier on a glass-silicon-glass sandwich. The quality of the mRNA is investigated with an Agilent 2100 bioanalyser using the RNA 6000 Nano Kit.

Figure 2A:
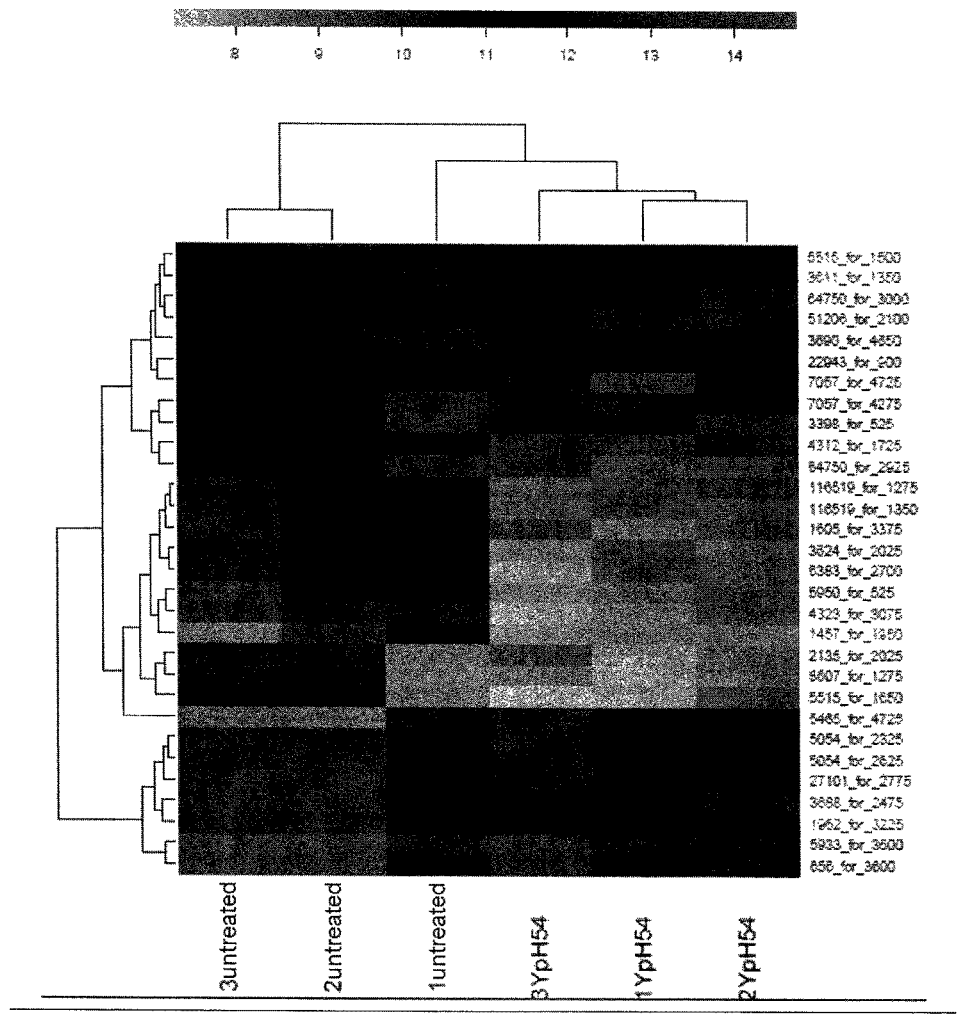
FIG. 2 shows two representative sets with chip data, as obtained using the protocol described. The data there were obtained by analysis of the markers of human fibroblasts, which were treated with extract from *Yarrowia* cells, which were cultured normally at pH 5.4 (FIG. 2a) or were exposed to stress at pH 2 (FIG. 2b).
Figure 2B:
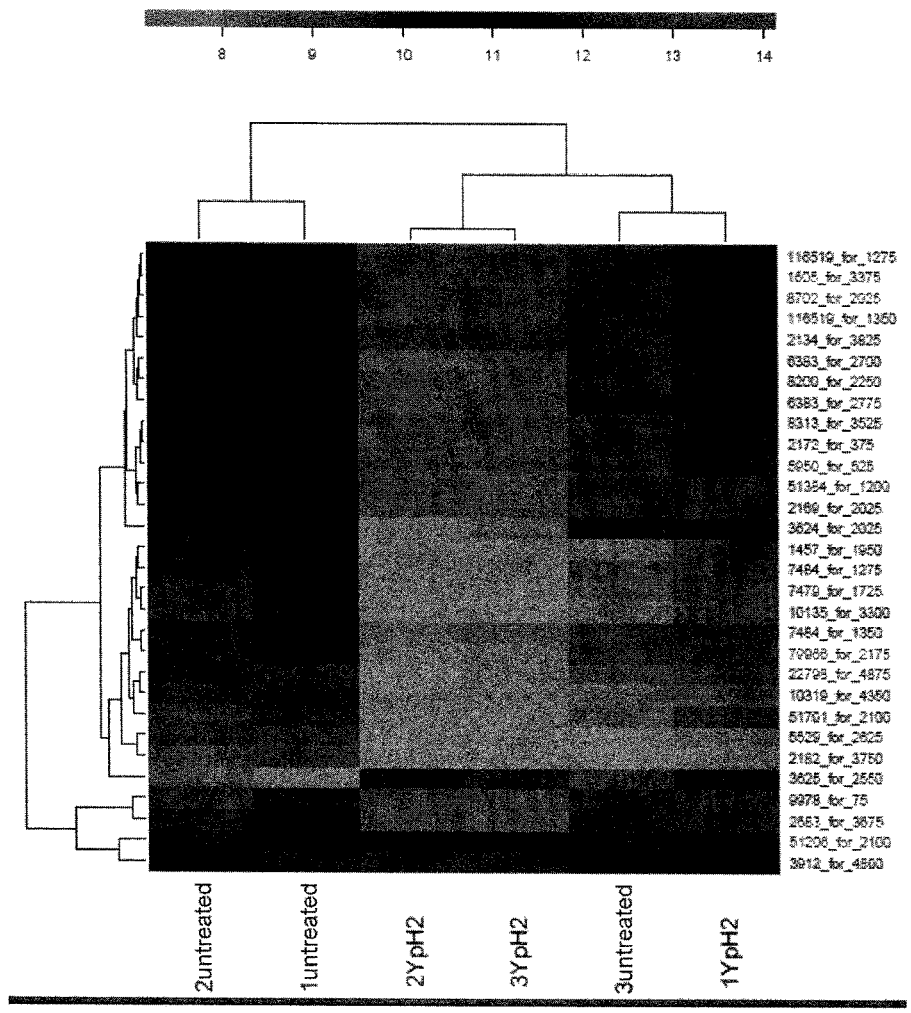

An example of two representative sets with chip data, obtained using the protocol described, is shown in FIGS. 2a and 2b. The data there were obtained by analysis of the markers of human fibroblasts that were treated with extract from Yarrowia cells that had been cultured normally at pH 5.4 (FIG. 2a) or had been exposed to stress at pH 2 (FIG. 2b).

The results of the tests are summarized in Table 2.

TABLE 2

Regulation of dermatologically relevant fibroblast markers after treatment with extracts of Saccharomyces cerevisiae cultures, which had been-stressed by increased temperature, treatment with hydrogen peroxide or exposure to medium with low pH.

| Yeast strain | Stress condition | Total number of induced or repressed markers | Number of strongly induced or repressed markers (≥2) |
|---|---|---|---|
| Saccharomyces cerevisiae | T | 273 | 1 |
| Saccharomyces cerevisiae | pH | 32 | 14 |
| Saccharomyces cerevisiae | $H_2O_2$ | 292 | 3 |

The different expression profiles of the cells treated with the extracts of variously stressed yeasts show that the yeast extracts have different properties and they are therefore different and distinguishable products.

EXAMPLE 3

Comparative Investigation of the Action of Extracts of pH-Stressed Cells of Different Yeast Genera on Human Fibroblasts The extent to which the cells of different yeast genera are suitable for producing dermatologically especially effective extracts was investigated.

The test conditions corresponded to those stated in example 2 for the production of extracts of pH-stressed cells, apart from the fact that extracts not only from one strain, but from Pichia CBS1991, Yarrowia lipolytica and Saccharomyces cerevisiae were contacted with human fibroblasts and their effects were compared.

TABLE 3

Regulation of dermatologically relevant fibroblast markers after treatment with extracts of cultures of different yeast strains, which had been stressed by exposure to medium with low pH.

| Yeast strain | pH | Type of regulation | Number of induced or repressed markers |
|---|---|---|---|
| Yarrowia lipolytica | 2 | Induced | 148 |
| | | Repressed | 65 |
| | 5.4 | Induced | — |
| | | Repressed | — |

TABLE 3-continued

Regulation of dermatologically relevant fibroblast markers after treatment with extracts of cultures of different yeast strains, which had been stressed by exposure to medium with low pH.

| Yeast strain | pH | Type of regulation | Number of induced or repressed markers |
|---|---|---|---|
| Saccharomyces cerevisiae | 2 | Induced | 31 |
| | | Repressed | 1 |
| | 5.4 | Induced | — |
| | | Repressed | — |
| Pichia CBS1991 | 3 | Induced | — |
| | | Repressed | — |
| | 5.4 | Induced | — |
| | | Repressed | — |

The results summarized in Table 3 show that the pH-stressed yeast cells of the genus *Yarrowia* have a particularly advantageous effect on the skin, in that in contact with human fibroblasts they regulate a particularly large number of skin markers positively.

EXAMPLE 4

Comparison of the Effect of Different Stress Conditions on Yeast Cells of the Genus *Yarrowia* with Respect to their Dermatological Efficacy After Processing to Extracts and Application on Human Fibroblasts After identifying yeast cells of the genus *Yarrowia* as a biotechnologically and dermatologically especially advantageous source of yeast extracts for skin applications, various stress conditions and combinations thereof were compared, with the following results, in order to find an especially advantageous method of production for these yeast extracts.

The extracts were in each case produced using a water-based and alcohol-based solvent, so as to be able to compare the respective effects.

TABLE 4

Regulation of dermatologically relevant fibroblast markers after treatment with extracts of *Yarrowia* cultures, which had been stressed under various stress conditions and combinations thereof.

| Test # | Stress condition(s) | Water (w) or propanediol (p) lysis | Type of regulation | Number of induced or repressed markers |
|---|---|---|---|---|
| 1 | — | w | Induced | 22 |
| 2 | | w | Repressed | 1 |
| 3 | — | p | Induced | 8 |
| 4 | | p | Repressed | — |
| 5 | 37° C. | w | Induced | 125 |
| 6 | | w | Repressed | 119 |
| 7 | 37° C. | p | Induced | 2 |
| 8 | | p | Repressed | 1 |
| 9 | pH 2 at 37° C. | w | Induced | 30 |
| 10 | | w | Repressed | 6 |
| 11 | pH 2 at 37° C. | p | Induced | 1 |
| 12 | | p | Repressed | — |
| 13 | pH 2 → 37° C. | w | Induced | 110 |
| 14 | | w | Repressed | 93 |
| 15 | pH 2 → 37° C. | p | Induced | 4 |
| 16 | | p | Repressed | 1 |
| 17 | 37° C. → pH 2 | w | Induced | 154 |
| 18 | | w | Repressed | 118 |
| 19 | 37° C. → pH 2 | p | Induced | 3 |
| 20 | | p | Repressed | 1 |

The results summarized in Table 4 show, firstly, that lysis of the cells using an aqueous solution is preferable to lysis using an alcoholic solution, as in the first case a much higher number of dermatologically relevant fibroblast markers is induced or repressed in a dermatologically advantageous direction.

Furthermore, it can be seen that the combination of stress factors of exposure to medium with low pH followed by temperature increase brings about the highest positive regulation of dermatologically relevant markers and is therefore preferable to other stress conditions or combinations thereof.

The invention claimed is:

1. A method of producing a dermatologically active yeast extract, said method comprising:
   providing a preculture of yeast cells selected from the group consisting of *Yarrowia, Saccharomyces*, and *Pichia* yeast cells;
   subjecting the preculture of yeast cells to an initial culturing step, wherein said initial culturing step is performed for at least 1 hour at a temperature of 34-39° C. and at a pH>5;
   culturing the yeast cells for at least fifteen minutes and at a pH of 1.8-4;
   harvesting the yeast cells; and
   lysing the yeast cells, wherein said lysis provides said yeast extract.

2. The method according to claim 1, wherein said lysing is carried out using a water-based lysis agent.

3. The method according to claim 1, wherein said culturing step is carried out at a temperature of 34-39° C.

4. The method according to claim 1, wherein said initial culturing step lasts 3-5 hours.

5. The method according to claim 1, wherein said culturing step lasts 45-75 minutes.

6. The method according to claim 1, wherein said initial culturing step and said culturing step are carried out at a temperature of 36-38° C.

7. The method according to claim 1, wherein said culturing step is carried out at a pH of 1.9-2.2.

8. The method according to claim 1, wherein said initial culturing step is carried out for 3-5 hours at a temperature of 36-38° C., said culturing step is carried out at a pH of 1.9-2.2, at a temperature of 36-38° C. and for 45-75 minutes and the yeast cells are yeast cells of the genus *Yarrowia*.

* * * * *